US006835469B2

(12) United States Patent
Kwong et al.

(10) Patent No.: US 6,835,469 B2
(45) Date of Patent: Dec. 28, 2004

(54) PHOSPHORESCENT COMPOUNDS AND DEVICES COMPRISING THE SAME

(75) Inventors: Raymond C. Kwong, Plainsboro, NJ (US); David B. Knowles, Apollo, PA (US); Mark E. Thompson, Anaheim, CA (US)

(73) Assignees: The University of Southern California, Los Angeles, CA (US); Universal Display Corporation, Ewing, NJ (US)

( * ) Notice: Subject to any disclaimer, the term of this patent is extended or adjusted under 35 U.S.C. 154(b) by 48 days.

(21) Appl. No.: 09/981,496

(22) Filed: Oct. 17, 2001

(65) Prior Publication Data

US 2003/0072964 A1 Apr. 17, 2003

(51) Int. Cl.[7] .................. H05B 33/14; C09K 11/06; C07D 215/00
(52) U.S. Cl. .................. 428/690; 428/917; 313/504; 546/4; 546/10
(58) Field of Search .................. 428/690, 917; 313/504, 506; 257/88, 102, 103; 546/4, 10; 252/301.16

(56) References Cited

U.S. PATENT DOCUMENTS

| | | | |
|---|---|---|---|
| 5,554,220 A | 9/1996 | Forrest et al. | 117/88 |
| 5,703,436 A | 12/1997 | Forrest et al. | 313/506 |
| 5,707,745 A | 1/1998 | Forrest et al. | 428/432 |
| 5,986,401 A | 11/1999 | Thompson et al. | 313/504 |
| 6,013,982 A | 1/2000 | Thompson et al. | 313/506 |
| 6,097,147 A | 8/2000 | Baldo et al. | 313/506 |
| 6,166,489 A | 12/2000 | Thompson et al. | 313/506 |
| 6,303,238 B1 | 10/2001 | Thompson et al. | 428/690 |
| 6,337,102 B1 | 1/2002 | Forrest et al. | 427/64 |
| 6,670,645 B2 * | 12/2003 | Grushin et al. | 257/98 |
| 2001/0019782 A1 | 9/2001 | Igarashi et al. | 428/690 |
| 2002/0034656 A1 * | 3/2002 | Thompson et al. | 428/690 |
| 2002/0121638 A1 * | 9/2002 | Grushin et al. | 257/40 |
| 2002/0182441 A1 * | 12/2002 | Lamansky et al. | 428/690 |
| 2002/0190250 A1 * | 12/2002 | Grushin et al. | 257/40 |
| 2003/0068526 A1 * | 4/2003 | Kamatani et al. | 428/690 |
| 2003/0108771 A1 * | 6/2003 | Lecloux et al. | 428/690 |

FOREIGN PATENT DOCUMENTS

| | | |
|---|---|---|
| WO | 00/57676 | 9/2000 |
| WO | 00/70655 | 11/2000 |
| WO | 01/41512 | 6/2001 |

OTHER PUBLICATIONS

Adachi, et al., "High–efficiency organic electrophosphorescent devices with tris(2–phenylpyridine)iridium doped into electron–transporting materials," *Appl. Phys. Lett.*, Aug. 2000, 77(6), 904–906.

Adachi et al., "High–efficiency red electrophosphorescence devices," *Appl. Phys. Lett.*, Mar. 2001, 78(11), 1622–1624.

Baldo et al., "Very high–efficiency green organic light–emitting devices based on electrophosphorescence," *Appl. Phys. Lett.*, Jul. 1999, 75(1), 4–6.

Baldo et al., "Highly efficient phosphorescent emission from organic electroluminescent devices," *Nature*, Sep. 1998, 395, 151–154.

Baldo et al., "Excitonic singlet–triplet ratio in a semiconducting organic thin film," *Phys. Rev. B*, Nov. 1999, 60(20), 14 422–14 428.

Burroughes et al., "Light–emitting diodes based on conjugated polymers," *Nature*, Oct. 1990, 347, 539–541.

(List continued on next page.)

*Primary Examiner*—Marie Yamnitzky
(74) *Attorney, Agent, or Firm*—Kenyon & Kenyon

(57) ABSTRACT

Phosphorescent organometallic complexes comprising phenylquinolinato ligands are provided. High efficiency organic light emitting devices comprising these compounds are also described.

2 Claims, 8 Drawing Sheets

Compound 1

Compound 2

Compound 3

Compound 4

Compound 5

Compound 6

OTHER PUBLICATIONS

Dartnall et al., "Human visual pigments: microspectrophotometric results from the eyes of seven person," *Proceedings of The Royal Society of London B*, 1983, 220, 115–130, (no month).

Gupta et al., "Absorption of Light by Visual Pigments: A Review of Theoretical Analyses," *Journal of Photochemistry*, 1985, 30, 173–206, (no month).

Hatwar et al., "Red Emitting Organic Electroluminescent Devices with Improved Stability," *Proceedings of the 10th International Workshop of Inorganic and Organic Electroluminescence*, Dec., 2000, Hamamatsu, Japan, 31–34.

Haworth, R. et al., "Synthetic Antimalarials. Part XXVII. Some Derivatives of Phthalazine, Quinoxaline, and iso-Quinoline," *J. Chem. Soc.*, 1948, 777–782, (no month).

Lamansky et al., "Synthesis and Characterization of Phosphorescent Cyclometalated Iridium Complexes," *Inorg. Chem.*, 2001, 40, 1704–1711 (published on Web Mar. 1, 2001).

Lamansky et al., "Highly Phosphorescent Bis–Cyclometalated Iridium Complexes: Synthesis, Photophysical Characterization, and Use in Organic Light Emitting Diodes," *J. Am. Chem. Soc.*, 2001, 123, 4304–4312 (published on Web Apr. 13, 2001).

Miyaura et al., "Palladium–Catalyzed Cross–Coupling Reactions of Organoboron Compounds," *Chem. Rev.* 1995, 2457–2483, vol. 95, No. 7, (no month).

Shoustikov et al., "Electroluminescence Color Tuning by Dye Doping in Organic Light–Emitting Diodes," *IEEE Journal of Selected Topics in Quantum Electronics*, Jan./Feb. 1998, 4(1), 3–13.

Silverstein, R.M. et al., *Spectrometric Identification of Organic Compounds*, Fifth Ed., p. 292, (date not given).

Solomons, T.W., *Organic Chemistry*, Fifth ed., pp. 654–661 (1992), (no month).

Tang et al., "Organic electroluminescent diodes," *Appl. Phys. Lett.* Sep. 1987, 51(12), 913–915.

\* cited by examiner

Compound 1

Compound 2

Compound 3

Compound 4

Compound 5

Compound 6

Compound 7

Compound 8

Compound 9

Compound 10

Compound 11

Compound 12

Compound 13

HOMO

LUMO

PHOSPHORESCENT COMPOUNDS AND DEVICES COMPRISING THE SAME

FIELD OF THE INVENTION

The present invention pertains to organometallic compounds and efficient organic light emitting devices comprising the same.

BACKGROUND OF THE INVENTION

Research Agreements

The claimed invention was made by, on behalf of, and/or in connection with one or more of the following parties to a joint university-corporation research agreement: Princeton University, The University of Southern California, and the Universal Display Corporation. The agreement was in effect on and before the date the claimed invention was made, and the claimed invention was made as a result of activities undertaken within the scope of the agreement.

Electronic display currently is a primary means for rapid delivery of information. Television sets, computer monitors, instrument display panels, calculators, printers, wireless phones, handheld computers, etc. aptly illustrate the speed, versatility, and interactivity that is characteristic of this medium. Of the known electronic display technologies, organic light emitting devices (OLEDs) are of considerable interest for their potential role in the development of full color, flat-panel display systems that may render obsolete the bulky cathode ray tubes still currently used in many television sets and computer monitors.

Generally, OLEDs are comprised of several organic layers in which at least one of the layers can be made to electroluminesce by applying a voltage across the device (see, e.g., Tang, et al., *Appl. Phys. Lett.* 1987, 51, 913 and Burroughes, et al., *Nature*, 1990, 347, 359). When a voltage is applied across a device, the cathode effectively reduces the adjacent organic layers (i.e., injects electrons) and the anode effectively oxidizes the adjacent organic layers (i.e., injects holes). Holes and electrons migrate across the device toward their respective oppositely charged electrodes. When a hole and electron meet on the same molecule, recombination is said to occur and an exciton is formed. Recombination of the hole and electron in luminescent compounds is accompanied by radiative emission, thereby producing electroluminescence.

Depending on the spin states of the hole and electron, the exciton which results from hole and electron recombination can have either a triplet or singlet spin state. Luminescence from a singlet exciton results in fluorescence whereas luminescence from a triplet exciton results in phosphorescence. Statistically, for organic materials typically used in OLEDs, one quarter of the excitons are singlets and the remaining three quarters are triplets (see, e.g., Baldo, et al., *Phys. Rev. B*, 1999, 60,14422). Until the discovery that there were certain phosphorescent materials that could be used to fabricate practical electro-phosphorescent OLEDs (U.S. Pat. No. 6,303,238) and, subsequently, demonstration such that electro-phosphorescent OLEDs could have a theoretical quantum efficiency of up to 100% (i.e., harvesting all of both triplets and singlets), the most efficient OLEDs were typically based on materials that fluoresced. Fluorescent materials luminesce with a maximum theoretical quantum efficiency of only 25% (where quantum efficiency of an OLED refers to the efficiency with which holes and electrons recombine to produce luminescence), since the triplet to ground state transition of phosphorescent emission is formally a spin forbidden process. Electro-phosphorescent OLEDs have now been shown to have superior overall device efficiencies as compared with electro-fluorescent OLEDs (see, e.g., Baldo, et al., *Nature*, 1998, 395, 151 and Baldo, e.g., *Appl. Phys. Lett.* 1999, 75(3), 4).

Due to strong spin-orbit coupling that leads to singlet-triplet state mixing, heavy metal complexes often display efficient phosphorescent emission from such triplets at room temperature. Accordingly, OLEDs comprising such complexes have been shown to have internal quantum efficiencies of more than 75% (Adachi, et al., *Appl. Phys. Lett.*, 2000, 77,904). Certain organometallic iridium complexes have been reported as having intense phosphorescence (Lamansky, et al., *Inorganic Chemistry*, 2001,40, 1704), and efficient OLEDs emitting in the green to red spectrum have been prepared with these complexes (Lamansky, et al., *J. Am. Chem. Soc.*, 2001, 123,4304). Red-emitting devices containing iridium complexes have been prepared according to U.S. Application Publication No. 2001/0019782. Phosphorescent heavy metal organometallic complexes and their respective devices have also been the subject of International Patent Application Publications WO 00/57676, WO 00/70655, and WO 01/41512; and U.S. Ser. Nos. 0/9274, 609, now abandoned; 09/452,346, now abandoned; 09/637, 766; 60/283,814; and U.S. Ser. No. 09/978,455, filed Oct. 16, 2001, entitled "Organometallic Compounds and Emission-Shifting Organic Electrophosphorescence" to Lamansky, et al.

Despite the recent discoveries of efficient heavy metal phosphors and the resulting advancements in OLED technology, there remains a need for even greater efficiency in devices. Fabrication of brighter devices that use less power and have longer lifetimes will contribute to the development of new display technologies and help realize the current goals toward full color electronic display on flat surfaces. The phosphorescent organometallic compounds, and the devices comprising them, described herein, help fulfill these and other needs.

SUMMARY OF THE INVENTION

In one aspect, the present invention provides compounds of Formula I, II, or III:

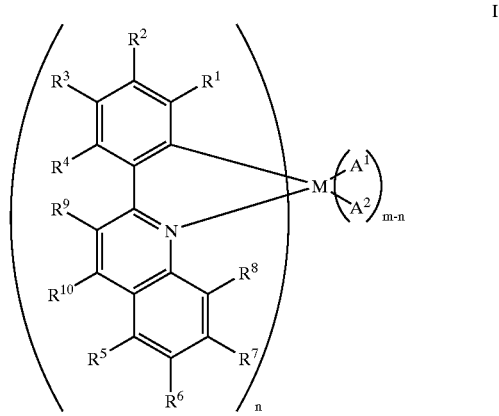

-continued

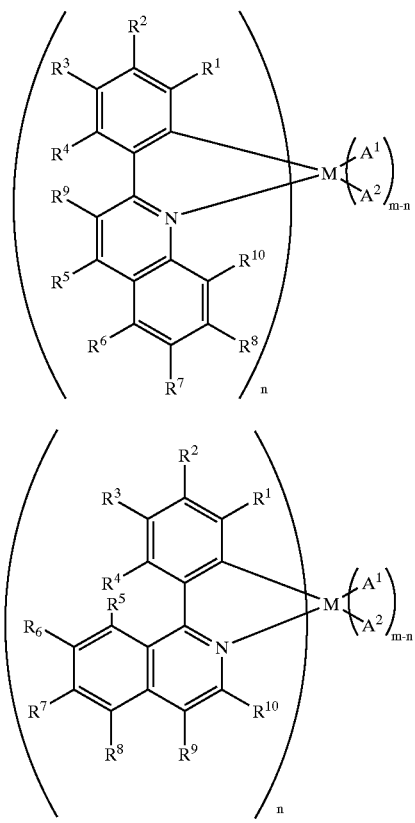

wherein:
M is a metal atom;
each $A^1$ and $A^2$ is, independently, a monodentate ligand; or $A^1$ and $A^2$ are covalently joined together to form a bidentate ligand;
each $R^1$, $R^2$, $R^3$, $R^4$, $R^5$, $R^6$, $R^7$, $R^8$, $R^9$, and $R^{10}$ is, independently, H, F, Cl, Br, I, $R^{11}$, $OR^{11}$, $N(R^{11})_2$, $P(R^{11})_2$, $P(OR^{11})_2$, $POR^{11}$, $PO_2R^{11}$, $PO_3R^{11}$, $SR^{11}$, $Si(R^{11})_3$, $B(R^{11})_2$, $B(OR^{11})_2$, $C(O)R^{11}$, $C(O)OR^{11}$, $C(O)N(R^{11})_2$, CN, $NO_2$, $SO_2$, $SOR^{11}$, $SO_2R^{11}$, $SO_3R^{11}$; and additionally, or alternatively, any one or more of $R^1$ and $R^2$, or $R^2$ and $R^3$, or $R^3$ and $R^4$, or $R^5$ and $R^6$, or $R^6$ and $R^7$, or $R^7$ and $R^8$, or $R^9$ and $R^{10}$, together form, independently, a fused 4- to 7-member cyclic group, wherein said cyclic group is cycloalkyl, cycloheteroalkyl, aryl, or heteroaryl, and wherein said cyclic group is optionally substituted by one or more substituents X;
each $R^{11}$ is, independently, H, $C_1$–$C_{20}$ alkyl, $C_2$–$C_{20}$ alkenyl, $C_2$–$C_{20}$ alkynyl, $C_1$–$C_{20}$ heteroalkyl, $C_3$–$C_{40}$ aryl, $C_3$–$C_{40}$ heteroaryl; wherein $R^{11}$ is optionally substituted by one or more substituents X;
each X is, independently, H, F, Cl, Br, I, $R^{12}$, $OR^{12}$, $N(R^{12})_2$, $P(R^{12})_2$, $P(OR^{12})_2$, $POR^{12}$, $PO_2R^{12}$, $PO_3R^{12}$, $SR^{12}$, $Si(R^{12})_3$, $B(R^{12})_2$, $B(OR^{12})_2$ $C(O)R^{12}$, $C(O)OR^{12}$, $C(O)N(R^{12})_2$, CN, $NO_2$, $SO_2$, $SOR^{12}$, $SO_2R^{12}$, or $SO_3R^{12}$;
each $R^{12}$ is, independently, H, $C_1$–$C_{20}$ alkyl, $C_1$–$C_{20}$ perhaloalkyl $C_2$–$C_{20}$ alkenyl, $C_2$–$C_{20}$ alkynyl, $C_1$–$C_{20}$ heteroalkyl, $C_3$–$C_{40}$ aryl, or $C_3$–$C_{40}$ heteroaryl;
m is the formal charge of metal atom M;

n is 1, 2 or 3; and
wherein at least one of $R^1$, $R^2$, $R^3$, $R^4$, $R^5$, $R^6$, $R^7$, $R^8$, $R^9$, and $R^{10}$ is not H in compounds of Formula I.

In some embodiments, M can be a heavy metal. In further embodiments, M can be Ir, Os, Pt, Pb, Re, or Ru; or M can be Ir; or M can be Pt. In further embodiments, $A^1$ and $A^2$ can be monodentate ligands which, in turn, can have a combined charge of (−1). In yet further embodiments, $A^1$ or $A^2$ can be F, Cl, Br, I, CO, CN, $CN(R^{11})$, $SR^{11}$ SCN, OCN, $P(R^{11})_3$, $P(OR^{11})_3$, $N(R^{11})_3$, NO, $N_3$, or a nitrogen-containing heterocycle optionally substituted by one or more substituents X. In further embodiments, $A^1$ and $A^2$ can be covalently joined together to form a bidentate ligand, which can be monoanionic. In some embodiments, the bidentate ligand can be

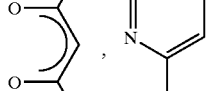

According to further embodiments, the bidentate ligand can coordinate through a carbon atom and a nitrogen atom. Further, the bidentate ligand can be a biaryl compound. In some embodiments, the bidentate ligand can be

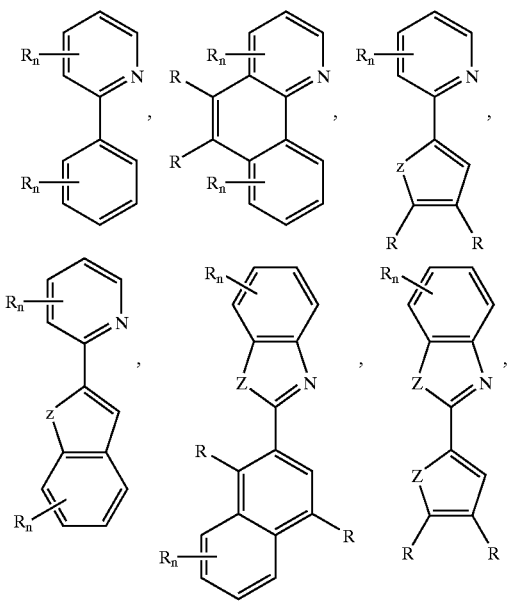

-continued

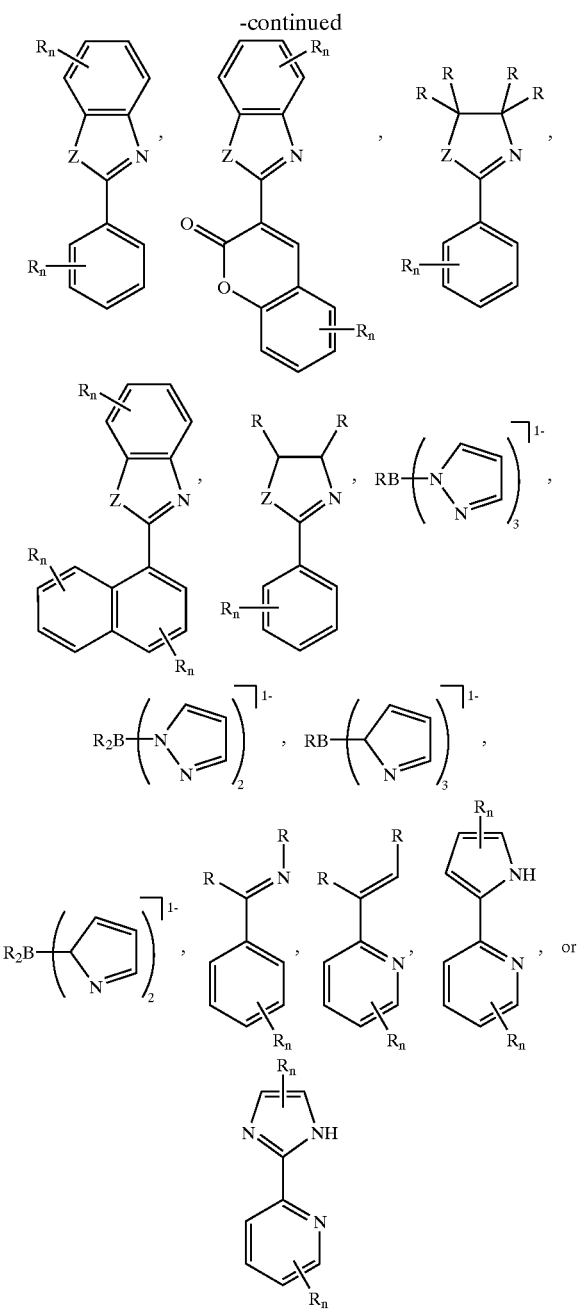

wherein:
Z is O, S, or NR;
each R is, independently, R$^{11}$; and
n is 0 to 5.

In some embodiments, bidentate ligand can be acetylacetonate.

In yet further embodiments, each R$^1$, R$^2$, R$^3$, R$^4$, R$^5$, R$^6$, R$^7$, R$^8$, R$^9$, and R$^{10}$ can be, independently, H, CH$_3$, CF$_3$, OCH$_3$, or F. In other embodiments, at least one of R$^1$, R$^2$, R$^3$, R$^4$, R$^5$, R$^6$, R$^7$, R$^8$, R$^9$, and R$^{10}$ is methyl. In other embodiments, at least one of R$^1$, R$^2$, R$^3$, R$^4$, R$^5$, R$^6$, R$^7$, R$^8$, R$^9$, and R$^{10}$ is trifluoromethyl. In other embodiments, at least one of R$^1$, R$^2$, R$^3$, R$^4$, R$^5$, R$^6$, R$^7$, R$^8$, R$^9$, and R$^{10}$ is methoxy. In other embodiments, at least one of R$^1$, R$^2$, R$^3$, R$^4$, R$^5$, R$^6$, R$^7$, R$^8$, R$^9$, and R$^{10}$ is fluoro. In other embodiments, at least one of said R$^3$, R$^4$, R$^9$, and R$^{10}$ is other than H.

According to some embodiments, compounds of the present invention can have a photoluminescence maximum at a wavelength of from about 550 to about 700 nm.

The present invention further includes compositions comprising a compound of Formula I, II, or III as described above. Compositions can further comprise BCP, CBP, OXD7, TAZ, CuPc, NPD, Alq$_3$, BAlq, FIrpic, or Irppy.

Also embodied by the present invention are compounds of Formula I

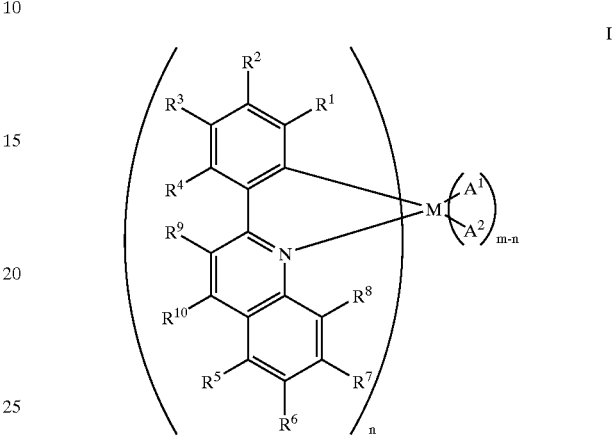

I wherein:
M is a metal atom;
each A$^1$ and A$^2$ is, independently, a monodentate ligand; or A$^1$ and A$^2$ are covalently joined together to form a bidentate ligand;
each R$^1$, R$^2$, R$^3$, R$^4$, R$^5$, R$^6$, R$^7$, R$^8$, R$^9$, and R$^{10}$ is, independently, H, an activating group, or a deactivating group; and additionally, or alternatively, any one or more of R$^1$ and R$^2$, or R$^2$ and R$^3$, or R$^3$ and R$^4$, or R$^5$ and R$^6$, or R$^6$ and R$^7$, or R$^7$ and R$^8$, or R$^9$ and R$^{10}$, together form, independently, a fused 4- to 7-member cyclic group, wherein said cyclic group is cycloalkyl, cycloheteroalkyl, aryl, or heteroaryl, and wherein said cyclic group is optionally substituted by one or more substituents X;
each X is, independently, H, F, Cl, Br, I, R$^{12}$, OR$^{12}$, N(R$^{12}$)$_2$, P(R$^{12}$)$_2$, P(OR$^{12}$)$_2$, POR$^{12}$, PO$_2$R$^{12}$, PO$_3$R$^{12}$, SR$^{12}$, Si(R$^{12}$)$_3$, B(R$^{12}$)$_2$, B(OR$^{12}$)$_2$C(O)R$^{12}$, C(O)OR$^{12}$, C(O)N(R$^{12}$)$_2$, CN, NO$_2$, SO$_2$, SOR$^{12}$, SO$_2$R$^{12}$, or SO$_3$R$^{12}$;
each R$^{12}$ is, independently, H, C$_1$–C$_{20}$ alkyl, C$_1$–C$_{20}$ perhaloalkyl C$_2$–C$_{20}$ alkenyl, C$_2$–C$_{20}$ alkynyl, C$_1$–C$_{20}$ heteroalkyl, C$_3$–C$_{40}$ aryl, or C$_3$–C$_{40}$ heteroaryl;
m is the formal charge of metal atom M;
n is 1, 2 or 3; and
wherein at least one of R$^3$, R$^9$, and R$^{10}$ is an activating group, or wherein at least one of R$^3$, R$^4$, R$^9$, and R$^{10}$ is a deactivating group.

According to some embodiments of the compounds of Formula I, at least one of R$^3$, R$^9$, and R$^{10}$ is an activating group. According to other embodiments of the compounds of Formula I at least one of R$^3$, R$^4$, R$^9$, and R$^{10}$ is a deactivating group. In some embodiments of the compounds of Formula I, activating groups can be alkyl, heteroalkyl, aryl, heteroaryl, alkoxy, aryloxy, hydroxy, mercapto, thiolato, amino, phosphino, alkylcarbonylamino, or arylcarbonylamino. In other embodiments of the compounds of Formula I, activating groups can be methyl or methoxy.

According to some embodiments of the compounds of Formula I, deactivating groups can be halo, cyano, nitro, aldehyde, alkylcarbonyl, arylcarbonyl, ammonium, perhaloalkyl, carboxylic acid, alkoxycarbonyl, aryloxycarbonyl, or sulfo. In other embodiments of the compounds of Formula I, deactivating group can be F or $CF_3$. In yet further embodiments of the compounds of Formula I, at least two of said $R^1$, $R^2$, $R^3$, $R^4$, $R^5$, $R^6$, $R^7$, $R^8$, $R^9$, and $R^{10}$ can be activating or deactivating groups.

Further embodiments of the compounds of Formula I include compounds where $A^1$ and $A^2$ are covalently joined together to form a bidentate ligand. The bidentate ligand can be monoanionic. The bidentate ligand can be acetylacetonate (acac), picolinate (pic), hexafluoroacetylacetonate, salicylidene, or 8-hydroxyquinolinate. In some embodiments, the bidentate ligand is acetylacetonate.

In yet further embodiments of the compounds of Formula I, M can be a heavy metal. In still further embodiments, M can be Ir, Os, Pt, Pb, Re, or Ru; or M can be Ir; or M can be Pt.

The present invention further includes compounds of Formula VI

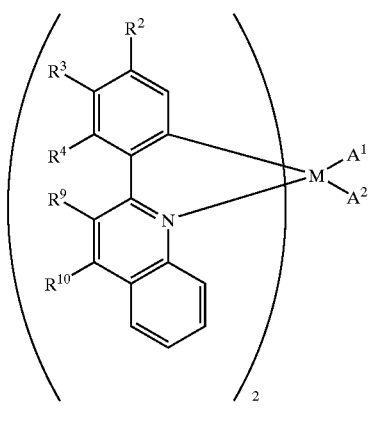

VI wherein:
M is a metal atom;
each $A^1$ and $A^2$ is, independently, a monodentate ligand; or $A^1$ and $A^2$ are covalently joined together to form a bidentate ligand; and
$R^4$ is F; and $R^2$, $R^3$, $R^9$, and $R^{10}$ are each, independently, H, an activating group or deactivating group; or
$R^4$ is $OCH_3$; and $R^2$, $R^3$, $R^9$, and $R^{10}$ are each, independently, H, an activating group or deactivating group; or
$R^3$ is $OCH_3$; and $R^2$, $R^4$, $R^9$, and $R^{10}$ are each, independently, H, an activating group or deactivating group; or
$R^2$ is $OCH_3$; and $R^3$, $R^4$, $R^9$, and $R^{10}$ are each, independently, H, an activating group or deactivating group; or
$R^4$ is $CF_3$; and $R^2$, $R^3$, $R^9$, and $R^{10}$ are each, independently, H, an activating group or deactivating group; or
$R^3$ is $CF_3$; and $R^2$, $R^4$, $R^9$, and $R^{10}$ are each, independently, H, an activating group or deactivating group; or
$R^2$ is $CF_3$; and $R^3$, $R^4$, $R^9$, and $R^{10}$ are each, independently, H, an activating group or deactivating group; or
$R^2$ and $R^4$ are each F; and $R^3$, $R^9$, and $R^{10}$ are each, independently, H, an activating group or deactivating group; or
$R^9$ is $CH_3$; and $R^2$, $R^3$, $R^4$, and $R^{10}$ are each, independently, H, an activating group or deactivating group; or
$R^{10}$ is $CH_3$; and $R^2$, $R^3$, $R^4$, and $R^9$ are each, independently, H, an activating group or deactivating group.

According to some embodiments of the compounds of Formula VI, $A^1$ and $A^2$ can be covalently joined together to form a bidentate ligand. In other embodiments of the compounds of Formula VI, the bidentate ligand can be monoanionic. In further embodiments of the compounds of Formula VI, bidentate ligand can be acetylacetonate (acac), picolinate (pic), hexafluoroacetylacetonate, salicylidene, or 8-hydroxyquinolinate. In yet further embodiments of the compounds of Formula VI, bidentate ligand can be acetylacetonate.

In some embodiments of the compounds of Formula VI, M can be a heavy metal; or M can be Ir, Os, Pt, Pb, Re, or Ru; or M can be Ir; or M can be Pt.

The present invention further includes compounds of Formula IV

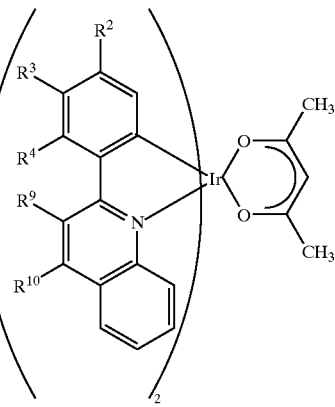

IV wherein:
$R^4$ is F; and $R^2$, $R^3$, $R^9$, and $R^{10}$ are each H; or
$R^4$ is $OCH_3$; and $R^2$, $R^3$, $R^9$, and $R^{10}$ are each H; or
$R^3$ is $OCH_3$; and $R^2$, $R^4$, $R^9$, and $R^{10}$ are each H; or
$R^2$ is $OCH_3$; and $R^3$, $R^4$, $R^9$, and $R^{10}$ are each H; or
$R^4$ is $CF_3$; and $R^2$, $R^3$, $R^9$, and $R^{10}$ are each H; or
$R^3$ is $CF_3$; and $R^2$, $R^4$, $R^9$, and $R^{10}$ are each H; or
$R^2$ is $CF_3$; and $R^3$, $R^4$, $R^9$, and $R^{10}$ are each H; or
$R^2$ and $R^4$ are each F; and $R^3$, $R^9$, and $R^{10}$ are each H; or
$R^4$ and $R^{10}$ are each $CH_3$; and $R^2$, $R^3$, and $R^9$ are each H; or
$R^9$ is $CH_3$; and $R^2$, $R^3$, $R^4$, and $R^{10}$ are each H; or
$R^{10}$ is $CH_3$; and $R^2$, $R^3$, $R^4$, and $R^9$ are each H.

In some embodiments of the compounds of Formula IV, $R^4$ is F; and $R^2$, $R^3$, $R^9$, and $R^{10}$ are each H. In other embodiments of the compounds of Formula IV, $R^4$ is $OCH_3$; and $R^2$, $R^3$, $R^9$, and $R^{10}$ are each H. In other embodiments of the compounds of Formula IV, $R^3$ is $OCH_3$; and $R^2$, $R^4$, $R^9$, and $R^{10}$ are each H. In other embodiments of the compounds of Formula IV, $R^2$ is $OCH_3$; and $R^3$, $R^4$, $R^9$, and $R^{10}$ are each H. In other embodiments of the compounds of Formula IV, $R^4$ is $CF_3$; and $R^2$, $R^3$, $R^9$, and $R^{10}$ are each H. In other embodiments of the compounds of Formula IV, $R^3$ is $CF_3$; and $R^2$, $R^4$, $R^9$, and $R^{10}$ are each H. In other embodiments of the compounds of Formula IV, $R^2$ is $CF_3$; and $R^2$, $R^4$, $R^9$, and $R^{10}$ are each H. In other embodiments of the compounds of Formula IV, $R^2$ and $R^4$ are each F; and $R^3$, $R^9$, and $R^{10}$ are each H. In other embodiments of the compounds of Formula IV, $R^4$ and $R^{10}$ are each $CH_3$; and $R^2$, $R^3$, and $R^9$ are each H. In other embodiments of the compounds of Formula IV, $R^9$ is $CH_3$; and $R^2$, $R^3$, $R^4$, and $R^{10}$ are each H. In other embodiments of the compounds of Formula IV, $R^{10}$ is $CH_3$; and $R^2$, $R^3$, $R^4$, and $R^9$ are each H.

The present invention further embodies compounds of Formula V

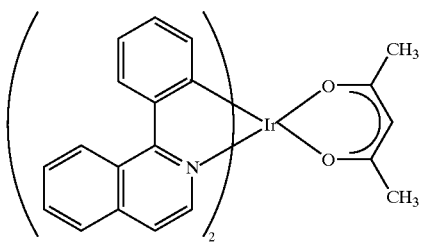

V.

The present invention further provides methods of increasing the wavelength of a photoluminescence maximum for compounds of the present invention, said methods comprising choosing substituents $R^1$, $R^2$, $R^3$, $R^4$, $R^5$, $R^6$, $R^7$, $R^8$, $R^9$, or $R^{10}$ such that at least one of said substituents is an activating group that influences the HOMO energy level of said compound, or at least one of said substituents is a deactivating group that influences the LUMO energy level of said compound.

The present invention further provides methods of decreasing the wavelength of a photoluminescence maximum for compounds of the present invention, said methods comprising choosing substituents $R^1$, $R^2$, $R^3$, $R^4$, $R^5$, $R^6$, $R^7$, $R^8$, $R^9$, or $R^{10}$ such that at least one of said substituents is a deactivating group that influences the HOMO energy level of said compound, or at least one of said substituents is an activating group that influences the LUMO energy level of said compound.

The present invention further includes organic light emitting devices comprising a compound of Formula I, II, or III

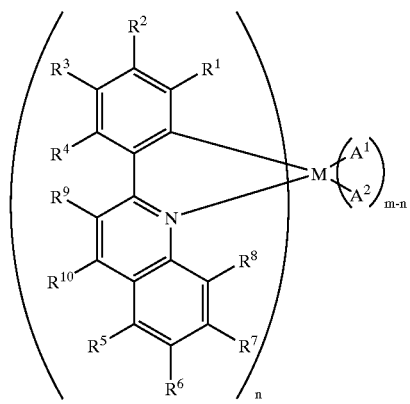

I

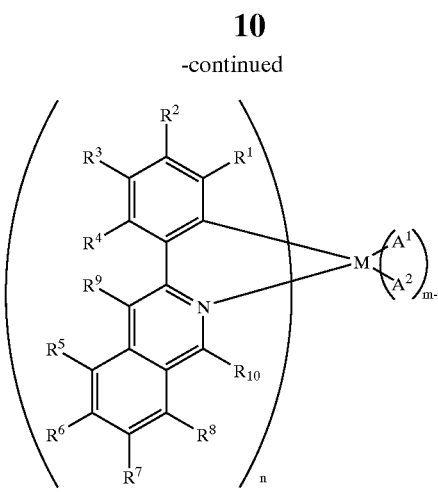

II

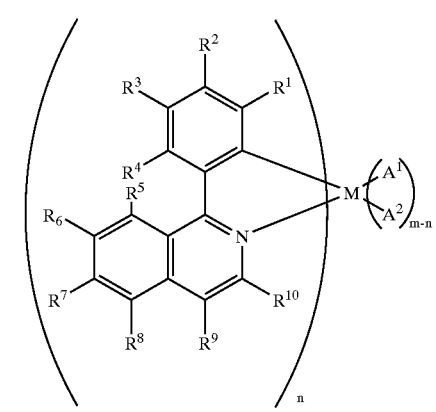

III wherein:
M is a metal atom;
each $A^1$ and $A^2$ is, independently, a monodentate ligand; or $A^1$ and $A^2$ are covalently joined together to form a bidentate ligand;
each $R^1$, $R^2$, $R^3$, $R^4$, $R^5$, $R^6$, $R^7$, $R^8$, $R^9$, and $R^{10}$ is, independently, H, F, Cl, Br, I, $R^{11}$, $OR^{11}$, $N(R^{11})_2$, $P(R^{11})_2$, $P(OR^{11})_2$, $POR^{11}$, $PO_2R^{11}$, $PO_3R^{11}$, $SR^{11}$, $Si(R^{11})_3$, $B(R^{11})_2$, $B(OR^{11})_2$, $C(O)R^{11}$, $C(O)OR^{11}$, $C(O)N(R^{11})_2$, CN, $NO_2$, $SO_2$, $SOR^{11}$, $SO_2R^{11}$, $SO_3R^{11}$; and additionally, or alternatively, any one or more of $R^1$ and $R^2$, or $R^2$ and $R^3$, or $R^3$ and $R^4$, or $R^5$ and $R^6$, or $R^6$ and $R^7$, or $R^7$ and $R^8$, or $R^9$ and $R^{10}$, together form, independently, a fused 4- to 7-member cyclic group, wherein said cyclic group is cycloalkyl, cycloheteroalkyl, aryl, or heteroaryl, and wherein said cyclic group is optionally substituted by one or more substituents X;
each $R^{11}$ is, independently, H, $C_1$–$C_{20}$ alkyl, $C_2$–$C_{20}$ alkenyl, $C_2$–$C_{20}$ alkynyl, $C_1$–$C_{20}$ heteroalkyl, $C_3$–$C_{40}$ aryl, $C_3$–$C_{40}$ heteroaryl; wherein $R^{11}$ is optionally substituted by one or more substituents X;
each X is, independently, H, F, Cl, Br, I, $R^{12}$, $OR^{12}$, $N(R^{12})_2$, $P(R^{12})_2$, $P(OR^{12})_2$, $POR^{12}$, $PO_2R^{12}$, $PO_3R^{12}$, $SR^{12}$, $Si(R^{12})_3$, $B(R^{12})_2$, $B(OR^{12})_2C(O)R^{12}$, $C(O)OR^{12}$, $C(O)N(R^{12})_2$, CN, $NO_2$, $SO_2$, $SOR^{12}$, $SO_2R^{12}$, or $SO_3R^{12}$;
each $R^{12}$ is, independently, H, $C_1$–$C_{20}$ alkyl, $C_1$–$C_{20}$ perhaloalkyl $C_2$–$C_{20}$ alkenyl, $C_2$–$C_{20}$ alkynyl, $C_1$–$C_{20}$ heteroalkyl, $C_3$–$C_{40}$ aryl, or $C_3$–$C_{40}$ heteroaryl;
m is the formal charge of metal atom M;

n is 1, 2 or 3; and wherein at least one of $R^1$, $R^2$, $R^3$, $R^4$, $R^5$, $R^6$, $R^7$, $R^8$, $R^9$, and $R^{10}$ is not H in compounds of Formula I.

According to some embodiments, devices can have compounds of Formula I, Formula II, or Formula III. In other embodiments, device can include an emissive layer comprising one or more compounds of the present invention. In further embodiments, the emissive layer consists essentially of one or more compounds of the present invention. In other embodiments, the emissive layer can comprise host material doped with compounds of the present invention. In some embodiments, compound of the present invention comprise from about 1 to about 20 wt % of the emissive layer. In other embodiments, host material comprises BCP, CBP, OXD7, TAZ, CuPc, NPD, $Alq_3$, or BAlq. In yet other embodiments, the emissive layer further comprises FIrpic or Irppy.

According to some embodiments, devices have an electroluminescence maximum of from about 550 to about 700 nm. In other embodiments, devices emit a color having color index coordinates (CIE) of from about 0.5 to about 0.8 for x and about 0.2 to about 0.5 for y. In yet further embodiments, devices have an external quantum efficiency greater than about 4% at a brightness greater than about 10 $cd/m^2$. In other embodiments, devices have an external quantum efficiency greater than about 4% at a brightness greater than about 100 $cd/m^2$.

In some embodiments, the present invention further provides organic light emitting devices comprising a compound of Formula I

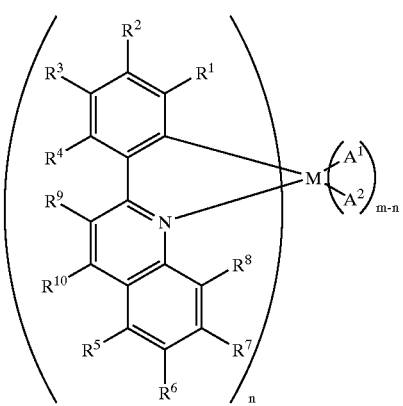

I wherein:

M is a metal atom;

each $A^1$ and $A^2$ is, independently, a monodentate ligand; or $A^1$ and $A^2$ are covalently joined together to form a bidentate ligand;

each $R^1$, $R^2$, $R^3$, $R^4$, $R^5$, $R^6$, $R^7$, $R^8$, $R^9$, and $R^{10}$ is, independently, H, an activating group, or a deactivating group; and additionally, or alternatively, any one or more of $R^1$ and $R^2$, or $R^2$ and $R^3$, or $R^3$ and $R^4$, or $R^5$ and $R^6$, or $R^6$ and $R^7$, or $R^7$ and $R^8$, or $R^9$ and $R^{10}$, together form, independently, a fused 4- to 7-member cyclic group, wherein said cyclic group is cycloalkyl, cycloheteroalkyl, aryl, or heteroaryl, and wherein said cyclic group is optionally substituted by one or more substituents X;

each X is, independently, H, F, Cl, Br, I, $R^{12}$, $OR^{12}$, $N(R^{12})_2$, $P(R^{12})_2$, $P(OR^{12})_2$, $POR^{12}$, $PO_2R^{12}$, $PO_3R^{12}$, $SR^{12}$, $Si(R^{12})_3$, $B(R^{12})_2$, $B(OR^{12})_2C(O)$ $R^{12}$, $C(O)OR^{12}$, $C(O)N(R^{12})_2$, CN, $NO_2$, $SO_2$, $SOR^{12}$, $SO_2R^{12}$, or $SO_3R^{12}$;

each $R^{12}$ is, independently, H, $C_1$–$C_{20}$ alkyl, $C_1$–$C_{20}$ perhaloalkyl $C_2$–$C_{20}$ alkenyl, $C_2$–$C_{20}$ alkynyl, $C_1$–$C_{20}$ heteroalkyl, $C_3$–$C_{40}$ aryl, or $C_3$–$C_{40}$ heteroaryl;

m is the formal charge of metal atom M;

n is 1, 2 or 3; and wherein at least one of $R^3$, $R^9$, and $R^{10}$ is an activating group, or wherein at least one of $R^3$, $R^4$, $R^9$, and $R^{10}$ is a deactivating group.

In some such embodiments, at least one of $R^3$, $R^9$, and $R^{10}$ is an activating group. In other such embodiments, at least one of $R^3$, $R^4$, $R^9$, and $R^{10}$ is a deactivating group. In further such embodiments, activating groups can be alkyl, heteroalkyl, aryl, heteroaryl, alkoxy, aryloxy, hydroxy, mercapto, thiolato, amino, phosphino, alkylcarbonylamino, or arylcarbonylamino. In yet further such embodiments, activating groups can be methyl or methoxy. According to some such embodiments, deactivating groups can be halo, cyano, nitro, aldehyde, alkylcarbonyl, arylcarbonyl, ammonium, perhaloalkyl, carboxylic acid, alkoxycarbonyl, aryloxycarbonyl, or sulfo. In other such embodiments, deactivating groups can be F or $CF_3$. In yet further such embodiments, at least two of said $R^1$, $R^2$, $R^3$, $R^4$, $R^5$, $R^6$, $R^7$, $R^8$, $R^9$, and $R^{10}$ are activating or deactivating groups.

According to some such embodiments, $A^1$ and $A^2$ can be covalently joined together to form a bidentate ligand. In some such embodiments, bidentate ligand can be monoanionic. In some such embodiments, bidentate ligand can be acetylacetonate (acac), picolinate (pic), hexafluoroacetylacetonate, salicylidene, or 8-hydroxyquinolinate. In some embodiments, bidentate ligand is acetylacetonate.

According to some such embodiments, M can be a heavy metal. In other such embodiments, M can be Ir, Os, Pt, Pb, Re, or Ru; or M can be Ir; or M can be Pt.

In some such embodiments, devices can include an emissive layer comprising compounds of the present invention. In some such embodiments, the emissive layer consists essentially of compounds of the present invention. In other such embodiments, the emissive layer comprises host material doped with compounds of the present invention. In further of such embodiments, compounds of the present invention can comprise from about 1 to about 20 wt % of the emissive layer. In some such embodiments, host material comprises BCP, CBP, OXD7, TAZ, CuPc, NPD, $Alq_3$, or BAlq. In other such embodiments, the emissive layer further comprises FIrpic or Irppy.

According to some such embodiments, devices can have an electroluminescence maximum of from about 550 to about 700 nm. In other embodiments, color emitted from such devices can have color index coordinates (CIE) of from about 0.5 to about 0.8 for x and about 0.2 to about 0.5 for y. In some embodiments, such devices can have an external quantum efficiency greater than about 4% at a brightness greater than about 10 $cd/m^2$. In other such embodiments, such devices can have an external quantum efficiency greater than about 4% at a brightness greater than about 100 $cd/m^2$.

Further embodiments of the present invention include organic light emitting devices comprising compounds of Formula VI

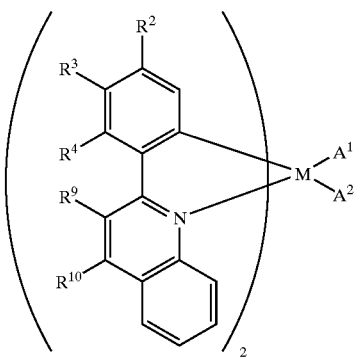

VI wherein:

M is a metal atom;

each $A^1$ and $A^2$ is, independently, a monodentate ligand; or $A^1$ and $A^2$ are covalently joined together to form a bidentate ligand; and $R^4$ is F; and $R^2$, $R^3$, $R^9$, and $R^{10}$ are each, independently, H, an activating group or deactivating group; or $R^4$ is $OCH_3$; and $R^2$, $R^3$, $R^9$, and $R^{10}$ are each, independently, H, an activating group or deactivating group; or $R^3$ is $OCH_3$; and $R^2$, $R^4$, $R^9$, and $R^{10}$ are each, independently, H, an activating group or deactivating group; or $R^2$ is $OCH_3$; and $R^3$, $R^4$, $R^9$, and $R^{10}$ are each, independently, H, an activating group or deactivating group; or $R^4$ is $CF_3$; and $R^2$, $R^3$, $R^9$, and $R^{10}$ are each, independently, H, an activating group or deactivating group; or $R^3$ is $CF_3$; and $R^2$, $R^4$, $R^9$, and $R^{10}$ are each, independently, H, an activating group or deactivating group; or $R^2$ is $CF_3$; and $R^3$, $R^4$, $R^9$, and $R^{10}$ are each, independently, H, an activating group or deactivating group; or $R^2$ and $R^4$ are each F; and $R^3$, $R^9$, and $R^{10}$ are each, independently, H, an activating group or deactivating group; or $R^9$ is $CH_3$; and $R^2$, $R^3$, $R^4$, and $R^{10}$ are each, independently, H, an activating group or deactivating group; or $R^{10}$ is $CH_3$; and $R^2$, $R^3$, $R^4$, and $R^9$ are each, independently, H, an activating group or deactivating group.

According to some such embodiments, $A^1$ and $A^2$ can be covalently joined together to form a bidentate ligand. In other such embodiments, bidentate ligand can be monoanionic. In some such embodiments, bidentate ligand is acetylacetonate (acac), picolinate (pic), hexafluoroacetylacetonate, salicylidene, or 8-hydroxyquinolinate. In yet other such embodiments, bidentate ligand can be acetylacetonate.

In some such embodiments, M can be a heavy metal; or M can be Ir, Os, Pt, Pb, Re, or Ru; or M can be Ir; or M can be Pt.

The present invention further includes organic light emitting devices comprising compounds of Formula IV

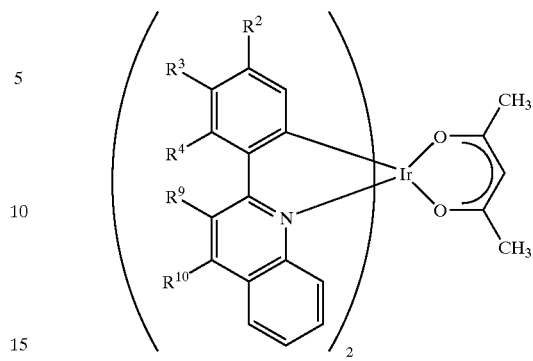

IV wherein:

$R^4$ is F; and $R^2$, $R^3$, $R^9$, and $R^{10}$ are each H; or
$R^4$ is $OCH_3$; and $R^2$, $R^3$, $R^9$, and $R^{10}$ are each H; or
$R^3$ is $OCH_3$; and $R^2$, $R^4$, $R^9$, and $R^{10}$ are each H; or
$R^2$ is $OCH_3$; and $R^2$, $R^4$, $R^9$, and $R^{10}$ are each H; or
$R^4$ is $CF_3$; and $R^2$, $R^3$, $R^9$, and $R^{10}$ are each H; or
$R^3$ is $CF_3$; and $R^2$, $R^4$, $R^9$, and $R^{10}$ are each H; or
$R^2$ is $CF_3$; and $R^3$, $R^4$, $R^9$, and $R^{10}$ are each H; or
$R^2$ and $R^4$ are each F; and $R^3$, $R^9$, and $R^{10}$ are each H; or
$R^4$ and $R^{10}$ are each $CH_3$; and $R^2$, $R^3$, and $R^9$ are each H; or
$R^9$ is $CH_3$; and $R^2$, $R^3$, $R^4$, and $R^{10}$ are each H; or
$R^{10}$ is $CH_3$; and $R^2$, $R^3$, $R^4$, and $R^9$ are each H.

In some such embodiments, $R^4$ is F; and $R^2$, $R^3$, $R^9$, and $R^{10}$ are each H. In other such embodiments, $R^4$ is $OCH_3$; and $R^2$, $R^3$, $R^9$, and $R^{10}$ are each H. In other such embodiments, $R^3$ is $OCH_3$; and $R^2$, $R^4$, $R^9$, and $R^{10}$ are each H. In other such embodiments, $R^2$ is $OCH_3$; and $R^3$, $R^4$, $R^9$, and $R^{10}$ are each H. In other such embodiments, $R^4$ is $CF_3$; and $R^2$, $R^3$, $R^9$, and $R^{10}$ are each H. In other such embodiments, $R^3$ is $CF_3$; and $R^2$, $R^4$, $R^9$, and $R^{10}$ are each H. In other such embodiments, $R^2$ is $CF_3$; and $R^3$, $R^4$, $R^9$, and $R^{10}$ are each H. In other such embodiments, $R^2$ and $R^4$ are each F; and $R^3$, $R^9$, and $R^{10}$ are each H. In other such embodiments, $R^4$ and $R^{10}$ are each $CH_3$; and $R^2$, $R^3$, and $R^9$ are each H. In other such embodiments, $R^9$ is $CH_3$; and $R^2$, $R^3$, $R^4$, and $R^{10}$ are each H. In other such embodiments, $R^{10}$ is $CH_3$; and $R^2$, $R^3$, $R^4$, and $R^9$ are each H.

The present invention further includes organic light emitting devices comprising compounds of Formula V

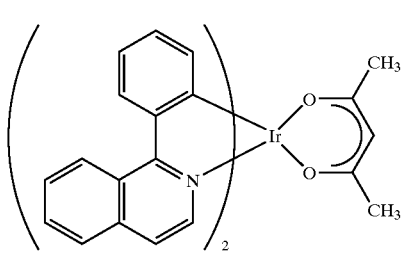

V.

The present invention further provides methods of increasing the wavelength of an electroluminescence maximum of an organic light emitting device comprising one or more compounds of the present invention, said methods comprising choosing substituents $R^1$, $R^2$, $R^3$, $R^4$, $R^5$, $R^6$, $R^7$, $R^8$, $R^9$, or $R^{10}$ such that at least one of said substituents is an activating group that influences the HOMO energy level of said compound, or at least one of said substituents is a deactivating group that influences the LUMO energy level of said compound.

The present invention further provides methods of decreasing the wavelength of an electroluminescence maximum of an organic light emitting device comprising one or more compounds of the present invention, said methods comprising choosing substituents $R^1$, $R^2$, $R^3$, $R^4$, $R^5$, $R^6$, $R^7$, $R^8$, $R^9$, or $R^{10}$ such that at least one of said substituents is a deactivating group that influences the HOMO energy level of said compound, or at least one of said substituents is an activating group that influences the LUMO energy level of said compound.

The present invention also provides pixels comprising devices of the present invention.

The present invention also provides electronic displays comprising devices of the present invention.

DETAILED DESCRIPTION OF PREFERRED EMBODIMENTS

Figure 1:
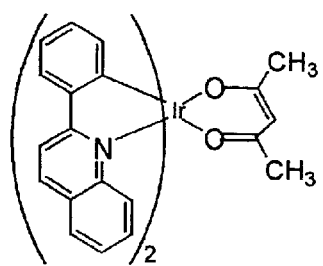
FIG. 1 shows structures of compounds 1 to 6.
Figure 1:
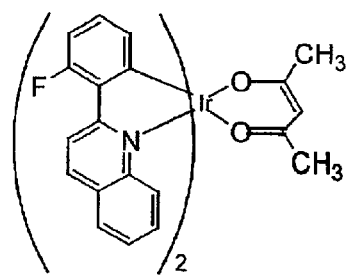
Figure 1:
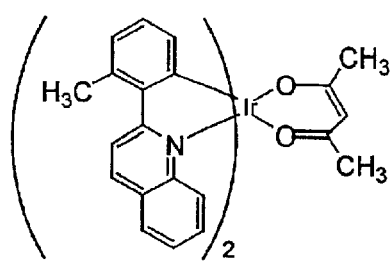
Figure 1:
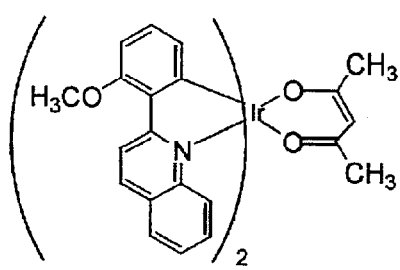
Figure 1:
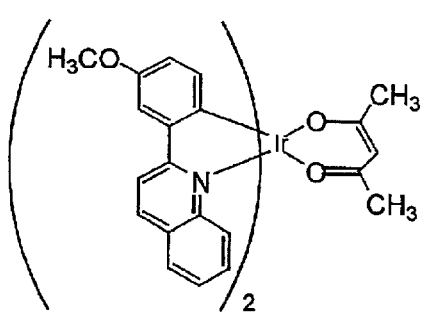
Figure 1:
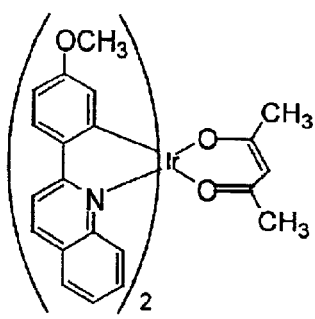

The present invention includes, inter alia, compounds of Formulas I, II, and III

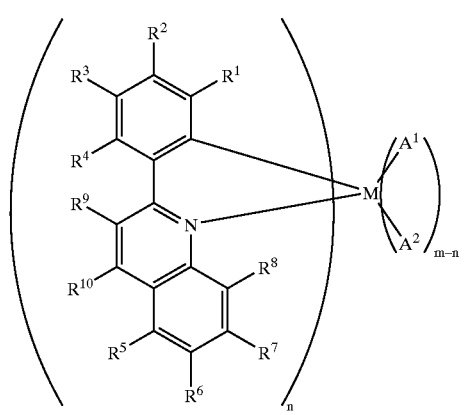

I

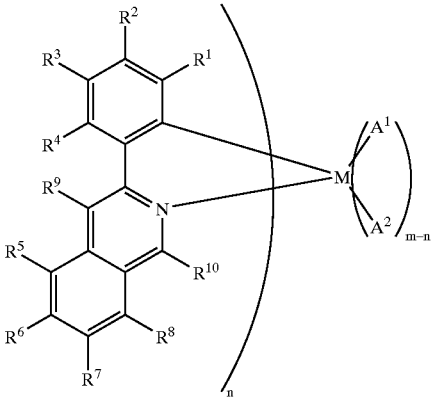

II

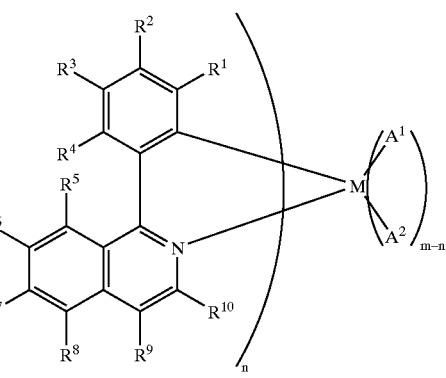

III wherein:
M is a metal atom;
each $A^1$ and $A^2$ is, independently, a monodentate ligand; or $A^1$ and $A^2$ are covalently joined together to form a bidentate ligand;
each $R^1$, $R^2$, $R^3$, $R^4$, $R^5$, $R^6$, $R^7$, $R^8$, $R^9$, and $R^{10}$ is, independently, H, F, Cl, Br, I, $R^{11}$, $OR^{11}$, $N(R^{11})_2$, $P(R^{11})_2$, $P(OR^{11})_2$, $POR^{11}$, $PO_2R^{11}$, $PO_3R^{11}$, $SR^{11}$, $Si(R^{11})_3$, $B(R^{11})_2$, $B(OR^{11})_2$, $C(O)R^{11}$, $C(O)OR^{11}$, $C(O)N(R^{11})_2$, CN, $NO_2$, $SO_2$, $SOR^{11}$, $SO_2R^{11}$, $SO_3R^{11}$; and additionally, or alternatively, any one or more of $R^1$ and $R^2$, or $R^2$ and $R^3$, or $R^3$ and $R^4$, or $R^5$ and $R^6$, or $R^6$ and $R^7$, or $R^7$ and $R^8$, or $R^9$ and $R^{10}$, together form, independently, a fused 4- to 7-member cyclic group, wherein said cyclic group is cycloalkyl, cycloheteroalkyl, aryl, or heteroaryl, and wherein said cyclic group is optionally substituted by one or more substituents X;
each $R^{11}$ is, independently, H, $C_1$–$C_{20}$ alkyl, $C_2$–$C_{20}$ alkenyl, $C_2$–$C_{20}$ alkynyl, $C_1$–$C_{20}$ heteroalkyl, $C_3$–$C_{40}$ aryl, $C_3$–$C_{40}$ heteroaryl; wherein $R^{11}$ is optionally substituted by one or more substituents X;
each X is, independently, H, F, Cl, Br, I, $R^{12}$, $OR^{12}$, $N(R^{12})_2$, $P(R^{12})_2$, $P(OR^{12})_2$, $POR^{12}$, $PO_2R^{12}$, $PO_3R^{12}$, $SR^{12}$, $Si(R^{12})_3$, $B(R^{12})_2$, $B(OR^{12})_2C(O)R^{12}$, $C(O)OR^{12}$, $C(O)N(R^{12})_2$, CN, $NO_2$, $SO_2$, $SOR^{12}$, $SO_2R^{12}$, or $SO_3R^{12}$;
each $R^{12}$ is, independently, H, $C_1$–$C_{20}$ alkyl, $C_1$–$C_{20}$ perhaloalkyl $C_2$–$C_{20}$ alkenyl, $C_2$–$C_{20}$ alkynyl, $C_1$–$C_{20}$ heteroalkyl, $C_3$–$C_{40}$ aryl, or $C_3$–$C_{40}$ heteroaryl;
m is the formal charge of metal atom M;
n is 1, 2 or 3; and wherein at least one of $R^1$, $R^2$, $R^3$, $R^4$, $R^5$, $R^6$, $R^7$, $R^8$, $R^9$, and $R^{10}$ is not H in compounds of Formula I. It is intended that the present compounds include any combination or $R^1$, $R^2$, $R^3$, $R^4$, $R^5$, $R^6$, $R^7$, $R^8$, $R^9$, $R^{10}$ substituents and fused cyclic groups.

According to compounds of the present invention, M can be any metal atom, including transition metals, lanthanides, actinides, main group metals, alkali metals and alkaline earth metals. Heavy metals provide thermal stability and superior phosphorescent properties to the present compounds and can include second and third row transition metals, lanthanides, actinides, as well as main group metals having atomic numbers greater than about 18. Second row transition metals include any of Zr, Nb, Mo, Tc, Ru, Rh, Pd, Ag, and Cd, and third row transistion metals include any of La, Hf, Ta, W, Re, Os, Ir, Pt, Au, and Hg. Main group metals having atomic numbers greater than 18 include Ga, Ge, In, Sn, Sb, Ti, Pb, Bi, and Po. In some embodiments, M is Ir, Os, Pt, Pb, Re, or Ru. In other embodiments, the metal atom is Ir. The metal atom M can have any formal charge designated as m. In some embodiments, the formal charge is positive such as 1+, 2+, 3+, 4+, 5+, 6+, 7+, or 8+. In further embodiments, formal charge is greater than 1+, in other embodiments, formal charge is greater than 2+, and in yet further embodiments, formal charge can be 3+.

Monodentate ligands $A^1$ and $A^2$ can include any ligand capable of coordinating to a metal atom through one atom. Numerous monodentate ligands are known to those skilled in the art and many suitable examples are provided in Cotton and Wilkinson, *Advanced Inorganic Chemistry*, Fourth Ed., John Wiley & Sons, New York, 1980, which is incorporated herein by reference in its entirety. In some embodiments, monodentate ligands can include F, Cl, Br, I, CO, CN, $CN(R^{11})$, $SR^{11}$ SCN, OCN, $P(R^{11})_3$, $P(OR^{11})_3$, $N(R^{11})_3$, NO, $N_3$, or a nitrogen-containing heterocycle optionally substituted by one or more substituents X. The phrase "nitrogen-containing heterocycle," as used herein refers to any heterocyclic group containing at least one nitrogen atom. Nitrogen-containing heterocycles can be saturated or unsaturated and include pyridine, imidazole, pyrrolidine, piperidine, morpholine, pyrimidine, pyrazine, pyridazine, pyrrole, 1,3,4-triazole, teterzole, isoxazole, thizole, derivatives thereof and the like. In further embodiments, one of $A^1$ and $A^2$ is a neutral monodentate ligand and the other of $A^1$ and $A^2$ is monoanionic, i.e., $A^1$ and $A^2$ have a combined charge of (−1). For example, $A^1$ can be chloro and $A^2$ can be pyridyl.

Figure 5:
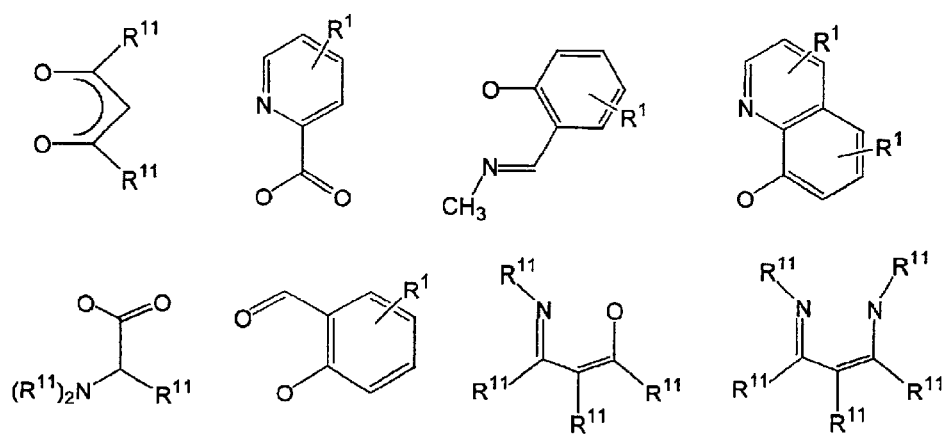
FIG. 5 shows structures of some bidentate ligands.
Figure 6:
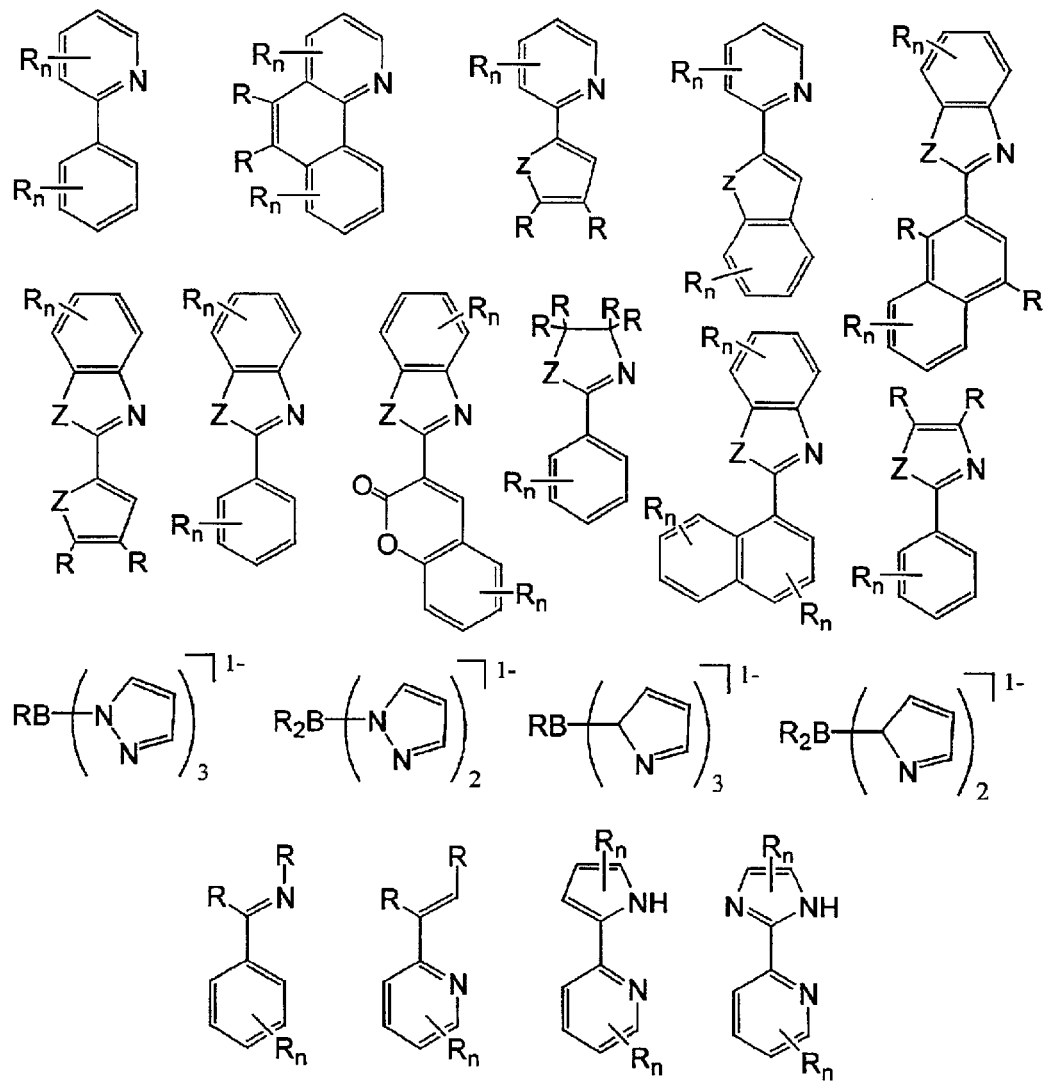
FIG. 6 shows structures of further bidentate ligands.

Together, $A^1$ and $A^2$ can also represent a bidentate ligand. Numerous bidentate ligands are known to those skilled in the art and many suitable examples are provided in Cotton and Wilkinson, *Advanced Inorganic Chemistry*, Fourth Ed., John Wiley & Sons, New York, 1980, which is incorporated herein by reference in its entirety. In some embodiments, bidentate ligands are monoanionic. Suitable bidentate ligands include acetylacetonate (acac), picolinate (pic), hexafluoroacetylacetonate, salicylidene, 8-hydroxyquinolinate; amino acids, salicylaldehydes, and iminoacetonates. Structure of some suitable bidentate ligands are provided in FIG. 5. Bidentate ligands can also include biaryl compounds. In some embodiments, the biaryl compounds coordinate to the metal atom through a carbon atom and a nitrogen atom. As used herein, the term "biaryl" refers to compounds comprising two aryl groups covalently joined by a single bond. The aryl groups of a biaryl compound can be aryl or heteroaryl, including both monocyclic or poly-cyclic aryl and heteroaryl groups. Examples of some biaryl groups are biphenyl, bipyridyl, phenylpyridyl, derivatives thereof and the like. Biaryl compounds can serve as bidentate ligands in metal coordination complexes, for instance, by coordinating though one atom in each of the two aryl groups. The coordinating atoms can be carbon or a heteroatom. Some further suitable bidentate ligands can include 2-(1-naphthyl)benzoxazole)), 2-phenylbenzoxazole, 2-phenylbenzothiazole, coumarin, thienylpyridine, phenylpyridine, benzothienylpyridine, 3-methoxy-2-phenylpyridine, thienylpyridine, tolylpyridine, phenylimines, vinylpyridines, arylquinolines, pyridylnaphthalenes, pyridylpyrroles, pyridylimidazoles, phenylindoles, derivatives thereof and the like. Further suitable bidentate ligands are provided in FIG. 6 (wherein Z is O, S, or NR; R is $R^{11}$; and n represents the number of substituents R ranging from, for example, 0 to 5) and in U.S. Ser. Nos. 09/274,609, now abandoned; 09/311,126, now abandoned; 09/452,346, now abandoned; 09/637,766; 60/283,814; and U.S. Ser. No. 09/978,455, filed Oct. 16, 2001, entitled "Organometallic Compounds and Emission-Shifting Organic Electrophosphorescence" to Lamansky, et al., each of which is incorporated herein by reference in its entirety.

Compounds of the present invention comprise at least one bidentate phenylquinolinato (pq) ligand. The term phenylquinolinato, or pq, is meant to refer to both substituted and non-substituted ligands, and the number (n) of coordinated pq ligands can be 1, 2, or 3. According to some embodiments, compounds of the present invention comprise m−1 pq ligands or, in some embodiments, two pq ligands. Phenylquinolinato ligands can be substituted with substituents $R^1$, $R^2$, $R^3$, $R^4$, $R^5$, $R^6$, $R^7$, $R^8$, $R^9$, and $R^{10}$ as defined above. Any combination of substituents is suitable. Substituents attached to adjacent carbon atoms of the pq ligands can, together, comprise a 4- to 7-member cyclic group that is fused to a ring of the ligand. For example, any or one or more of the pairs $R^1$ and $R^2$, or $R^2$ and $R^3$, or $R^3$ and $R^4$, or $R^5$ and $R^6$, or $R^6$ and $R^7$, or $R^7$ and $R^8$, or $R^9$ and $R^{10}$ can comprise a fused cyclic group. The phrase "fused cyclic group" refers to a cyclic group that shares one or more bonds with a further cyclic group. Phenylquinolinato ligands of compounds of the present invention can have any number of fused cyclic group substituents, including 0, 1, 2, 3, 4, or 5 fused cyclic groups. Any feasible combination of fused cyclic groups and the remaining of $R^1$, $R^2$, $R^3$, $R^4$, $R^5$, $R^6$, $R^7$, $R^8$, $R^9$, and $R^{10}$ that are not involved in a fused cyclic group are embodied by the present invention. In some embodiments of the present invention, at least one of $R^1$, $R^2$, $R^3$, $R^4$, $R^5$, $R^6$, $R^7$, $R^8$, $R^9$, and $R^{10}$ is not H for compounds of Formula I. In some embodiments of the present invention, at least one of $R^1$, $R^2$, $R^3$, $R^4$, $R^5$, $R^6$, $R^7$, $R^8$, $R^9$, and $R^{10}$ is not H for compounds of Formula II. In some embodiments of the present invention, at least one of $R^1$, $R^2$, $R^3$, $R^4$, $R^5$, $R^6$, $R^7$, $R^8$, $R^9$, and $R^{10}$ is not H for compounds of Formula III. In further embodiments, any of $R^1$, $R^2$, $R^3$, $R^4$, $R^5$, $R^6$, $R^7$, $R^8$, $R^9$, and $R^{10}$ can be H, methyl ($CH_3$), trifluoromethyl ($CF_3$), methoxy ($OCH_3$), or fluoro (F), and in other embodiments, at least one of $R^1$, $R^2$, $R^3$, $R^4$, $R^5$, $R^6$, $R^7$, $R^8$, $R^9$, and $R^{10}$ is $CH_3$, $CF_3$, $OCH_3$, or F. Additionally, any of $R^1$, $R^2$, $R^3$, $R^4$, $R^5$, $R^6$, $R^7$, $R^8$, $R^9$, and $R^{10}$ can be H, an activating group, or a deactivating group. In yet further embodiments, at least one of $R^3$, $R^4$, $R^9$, and $R^{10}$ is a substituent other than H.

The present invention further includes compounds of Formula I where M, $A^1$, $A^2$, m, and n are as hereinbefore defined and each $R^1$, $R^2$, $R^3$, $R^4$, $R^5$, $R^6$, $R^7$, $R^8$, $R^9$, and $R^{10}$ is, independently, H, an activating group, or a deactivating group; and additionally, or alternatively, any one or more of $R^1$ and $R^2$, or $R^2$ and $R^3$, or $R^3$ and $R^4$, or $R^5$ and $R^6$, or $R^6$ and $R^7$, or $R^7$ and $R^8$, or $R^9$ and $R^{10}$, together form, independently, a fused 4- to 7-member cyclic group, wherein the cyclic group is cycloalkyl, cycloheteroalkyl, aryl, or heteroaryl, and wherein the cyclic group is optionally substituted by one or more substituents X; and wherein at least one of $R^3$, $R^9$, and $R^{10}$ is an activating group or a deactivating group, or wherein at least one of $R^3$, $R^4$, $R^9$, and $R^{10}$ is a deactivating group.

The present invention further includes compounds of Formula VI

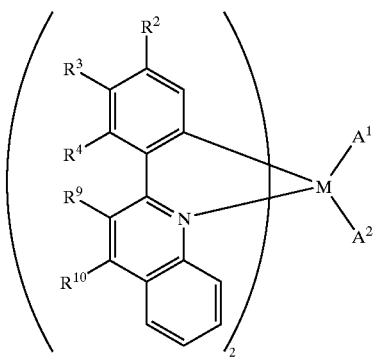

wherein M, $A^1$, $A^2$, are as hereinbefore defined. According to Formula VI, $R^4$ can be F and $R^2$, $R^3$, $R^9$, and $R^{10}$ can each, independently, be H, an activating group or deactivating group; or $R^4$ can be $OCH_3$ and $R^2$, $R^3$, $R^9$, and $R^{10}$ can each, independently, be H, an activating group or deactivating group; or $R^3$ is $OCH_3$ and $R^2$, $R^4$, $R^9$, and $R^{10}$ can each, independently, be H, an activating group or deactivating group; or $R^2$ can be $OCH_3$ and $R^3$, $R^4$, $R^9$, and $R^{10}$ can each, independently, be H, an activating group or deactivating group; or $R^4$ can be $CF_3$; and $R^2$, $R^3$, $R^9$, and $R^{10}$ can each, independently, be H, an activating group or deactivating group; or $R^3$ can be $CF_3$ and $R^2$, $R^4$, $R^9$, and $R^{10}$ can each, independently, be H, an activating group or deactivating group; or $R^2$ can be $CF_3$ and $R^3$, $R^4$, $R^9$, and $R^{10}$ can each, independently, be H, an activating group or deactivating group; or $R^2$ and $R^4$ can each be F and $R^3$, $R^9$, and $R^{10}$ can each, independently, be H, an activating group or deactivating group; or $R^9$ can be $CH_3$ and $R^2$, $R^3$, $R^4$, and $R^{10}$ can each be, independently, be H, an activating group or deactivating group; or $R^{10}$ is $CH_3$; and $R^2$, $R^3$, $R^4$, and $R^9$ can each, independently, be H, an activating group or deactivating group.

The present invention further includes compounds of Formula IV.

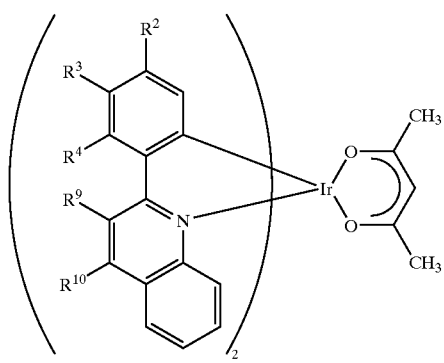

Figure 2:
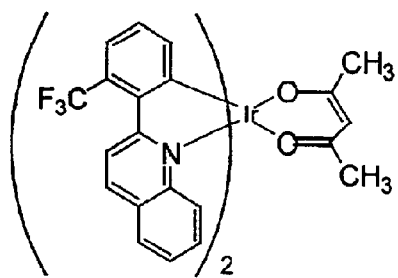
FIG. 2 shows structures of compounds 7 to 13.
Figure 2:
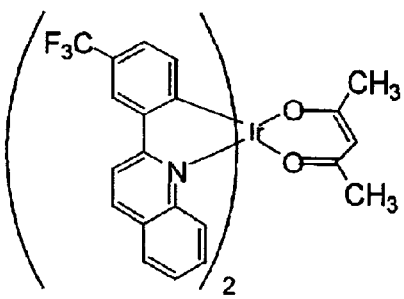
Figure 2:
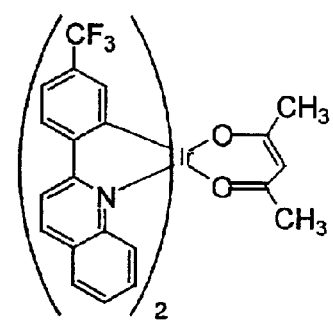
Figure 2:
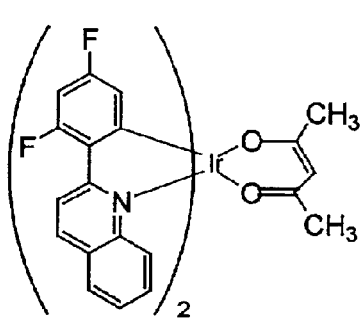
Figure 2:
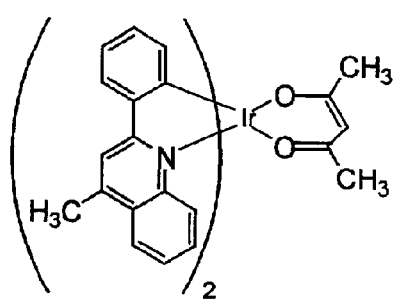
Figure 2:
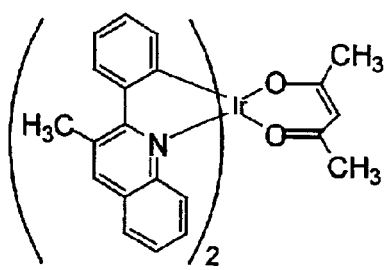
Figure 2:
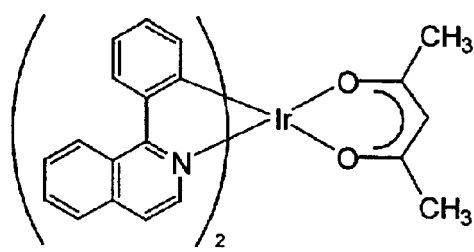

According to Formula IV, compounds of the present invention include those where $R^4$ is F; and $R^2$, $R^3$, $R^9$, and $R^{10}$ are each H (compound 2); or $R^4$ is $OCH_3$; and $R^2$, $R^3$, $R^9$, and $R^{10}$ are each H (compound 4); or $R^3$ is $OCH_3$; and $R^2$, $R^4$, $R^9$, and $R^{10}$ are each H (compound 5); or $R^2$ is $OCH_3$; and $R^3$, $R^4$, $R^9$, and $R^{10}$ are each H (compound 6); or $R^4$ is $CF_3$; and $R^2$, $R^3$, $R^9$, and $R^{10}$ are each H (compound 7); or $R^3$ is $CF_3$; and $R^2$, $R^4$, $R^9$, and $R^{10}$ are each H (compound 8); or $R^2$ is $CF_3$; and $R^3$, $R^4$, $R^9$, and $R^{10}$ are each H (compound 9); or $R^2$ and $R^4$ are each F; and $R^3$, $R^9$, and $R^{10}$ are each H (compound 10); or $R^4$ and $R^{10}$ are each $CH_3$; and $R^2$, $R^3$, and $R^9$ are each H; or $R^9$ is $CH_3$; and $R^2$, $R^3$, $R^4$, and $R^{10}$ are each H (compound 11); or $R^{10}$ is $CH_3$; and $R^2$, $R^3$, $R^4$, and $R^9$ are each H (compound 12). Structures of some of these compounds and others are provided in FIGS. 1 and 2.

Also embodied by the present invention is a compound of Formula V (compound 13).

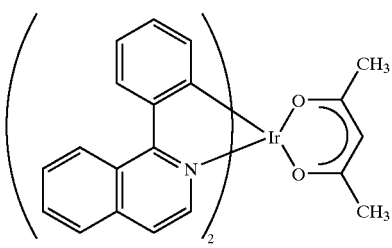

Activating and deactivating groups are well recognized by those skilled in the art, and/or can be readily identified by routine measurements. As is well understood according to theory, activating and deactivating groups are so named for their respective abilities to stabilize or destabilize the arenium ion intermediate state in electrophilic substitution reactions of aromatic compounds and to direct orientation (i.e., ortho-para vs. meta directors). The activating or deactivating ability of a particular substituent is governed by several factors including the inductive effect and resonance effect. Not wishing to be bound by any particular theory, it is believed that the inductive effect arises from the electrostatic interaction of the substituent with the molecule to which the substituent is attached. For example, if the substituent is more electronegative than the atom to which it is attached, the substituent inductively draws electron density away from the molecule. Substituents having higher electronegativity have stronger inductive effects. Substituents bearing a full or partial charge also tend to withdraw electron density inductively. On the other hand, the resonance effect relates to the contribution of a substituent to resonance stabilization of a molecule. For example, it is believed that a substituent having a lone pair of electrons can contribute to further resonance structures by delocalization of the lone pair onto an aromatic molecule.

Varying contributions of inductive and resonance effects help determine the activating or deactivating abilities of a substituent. A substituent that is deactivating tends to destabilize the arenium ion intermediate of electrophilic subsitution by withdrawing electron density from the molecule such as through the inductive effect. Thus, strongly electronegative substituents, such as halogens, can be considered deactivating since destablilizing inductive effects can dominate over stabilizing resonance effects. Weaker electronegative substituents, such as hydroxyl or methoxy, can be considered activating since resonance effects involving the oxygen lone pair tend to dominate over deactivating inductive effects. Although alkyl groups lack a lone pair to contribute to resonance stabilization, they are typically considered activating groups due to hyperconjugation.

Some suitable activating groups include, for example, alkyl, heteroalkyl, aryl, heteroaryl, alkoxy, aryloxy, hydroxy, mercapto, thiolato, amino, phosphino, alkylcarbonylamino, arylcarbonylamino, and the like. As an example, methyl and methoxy can serve as activating groups. Some suitable activating groups have a lone pair of electrons (e.g., alkoxy, amino, etc.) Some suitable deactivating groups include, for example, halo, cyano, nitro, aldehyde, alkylcarbonyl, arylcarbonyl, ammonium, perhaloalkyl, carboxylic acid, alkoxycarbonyl, aryloxycarbonyl, sulfo ($SO_3H$), and the like. As an example, fluoro and trifluoromethyl can serve as deactivating groups. Activating and deactivating groups are treated in detail, for example, in T. W. Graham Solomons, *Organic Chemistry*, Fifth ed., pp. 654–661 (1992), which is incorporated herein by reference in its entirety.

As used herein, the term "alkyl" includes linear, branched, and cyclic alkyl groups. In some embodiments, alkyl groups are $C_1$–$C_{20}$ alkyl groups. Examples of alkyl groups include, methyl, ethyl, n-propyl, isopropyl, n-butyl, isobutyl, cyclohexyl, norbornyl, and the like. As used herein, the term "heteroalkyl" refers to alkyl groups including one or more heteroatoms such as O, S, or N. Heteroalkyl groups can also comprise unsaturations. Examples of heteroalkyl groups include pyrrolidinyl, piperidinyl, morpholinyl, and the like. The term "perhaloalkyl" refers to alkyl groups substituted by halogen. Examples of a perhaloalkyl group include trifluoromethyl, trichloromethyl, pentafluoroethyl, and the like. "Alkenyl" groups refer to alkyl groups having one or more double bonds, and "alkynyl" groups refer to alkyl groups having one or more triple bonds. "Alkoxy" groups can have from about 1 to about 20 carbon atoms and can include, for example, methoxy, ethoxy, propoxy, n-butoxy, isobutoxy, and the like. "Aryloxy" groups can have from about 3 to about 40 carbon atoms and can include, for example, phenoxy and the like. "Aryl" groups can be any mono- or polycyclic aromatic group, and "heteroaryl" refers to an aryl group including one or more heteroatoms such as O, S, or N. Aryl groups can have 3 to about 40 carbon atoms and can include, for example, phenyl, 4-methylphenyl, naphthyl, anthracenyl, phenanthryl, and the like. Heteroaryl groups can include, for example, pyridyl, indolyl, benzothiophene, quinolinyl, and the like. "Amino" groups, as used herein, include amino, alkylamino, dialkylamino, arylamino, and diarylamino groups. Examples of amino groups include, $NH_2$, methylamino, dimethylamino, phenylamino, diphenylamino, and the like. "Phosphino" groups, as used herein, include phosphino, alkylphosphino, dialkylphosphino, arylphosphino, and diarylphosphino. Some examples of phosphino groups include $PH_2$, methylphosphino, dimethylphosphino, phenylphosphino, diphenylphosphino, and the like. "Thiolato" groups can have from about 1 to about 20 carbon atoms and can include, for example, thiomethoxy, thiophenoxy, and the like. "Halo" groups include fluoro, chloro, bromo, and iodo, for instance.

The compounds of the present invention can be photoluminescent. In some embodiments, the present compounds are efficient phosphors, having, for example, a significant portion of luminescence arising from phosphorescent emission. The compounds can emit at any color, including red, green, blue, and other colors (i.e., red-orange, blue-green, etc.). In some embodiments, the emission can be red or reddish. Color of emission can be estimated from the photoluminescence spectrum. A luminescence maximum of from about 550 to about 700 nm can indicate red or reddish emission. A maximum at lower wavelengths can indicate green or blue emission. Additionally, the color of emission for compounds of the present invention can be described by color index coordinates x and y (Commision Internationale de L'Eclairage (CIE) 1931 standard 2-degree observer; see, e.g., Shoustikov, et al., *IEEE Journal of Selected Topics in Quantum Electronics*, 1998, 4, 3; Dartnall, et al., *Proceedings of the Royal Society of London B*, 1983, 220, 115; Gupta, et al., *Journal of Photochemistry*, 1985, 30, 173; *Colorimetry*, $2^{nd}$ ed., Publication CIE 15.2-1986 (ISBN 3-900-734-00-3). For example, a compound emitting in the reds can have coordinates of from about 0.5 to about 0.8 for x and 0.2 to about 0.5 for y. Any set of color coordinates can be within reach of the compounds of the present invention.

Figure 7:
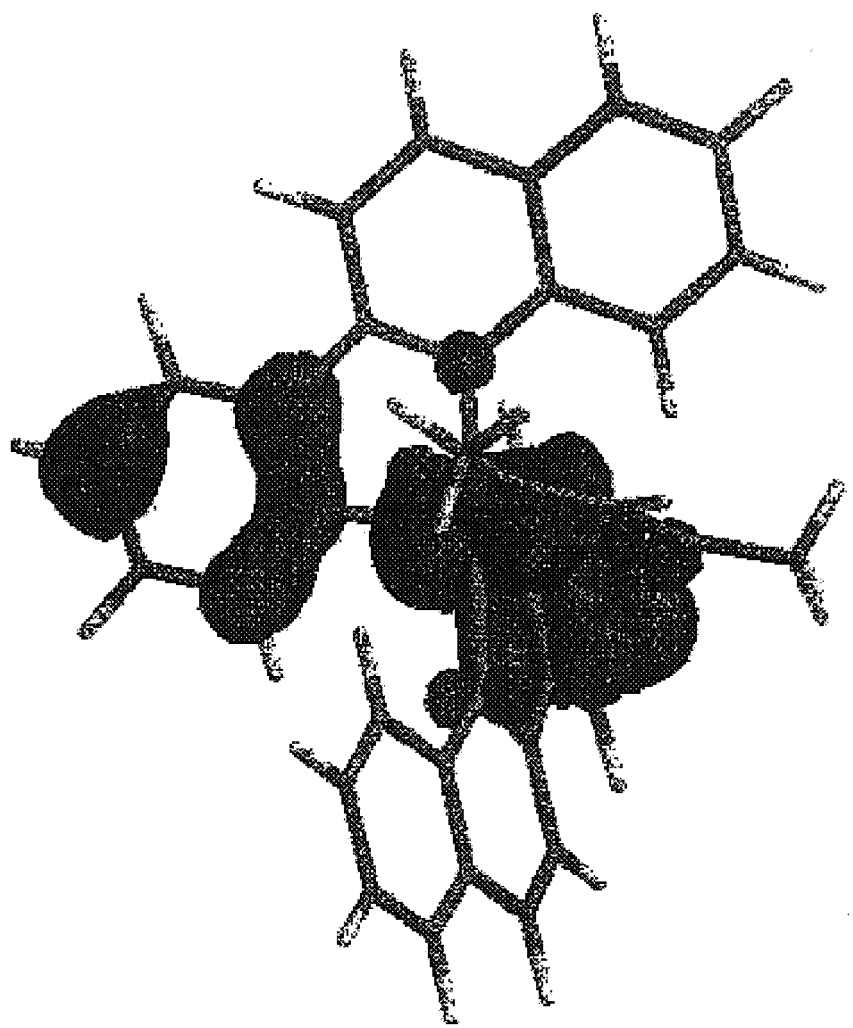
FIG. 7 illustrates the HOMO calculated for bis(phenylquinolinato)iridium(III) acetylacetonate compounds.
Figure 8:
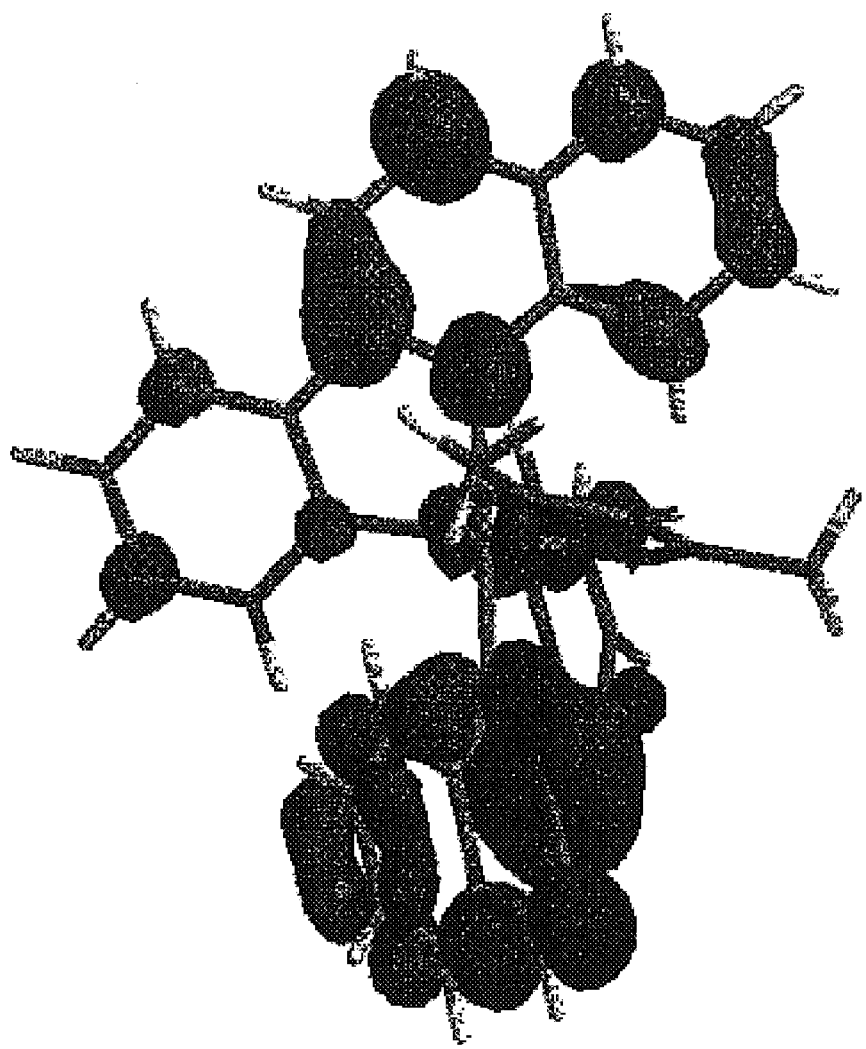
FIG. 8 illustrates the LUMO calculated for bis(phenylquinolinato)iridium(III) acetylacetonate compounds.

Substitution of the phenylquinolinato ligand by various substituents $R^1$, $R^2$, $R^3$, $R^4$, $R^5$, $R^6$, $R^7$, $R^8$, $R^9$, and $R^{10}$, can affect emission color. In fact, emission color can be deliberately controlled, or "tuned," in compounds of the present invention by judicious selection of substituents. Since emission color is sensitive to the energy gap between the HOMO and LUMO energy levels of the compound, substituents that predictably affect either or both of these molecular orbitals can be purposefully incorporated into compounds of the present invention to achieve a certain color. For example, molecular orbital (MO) calculations can help indicate which carbon atoms of the phenyl and quinolinyl moieties of the ligand contribute to the HOMO or LUMO. Results from an example MO calculation for a bis(phenylquinolinato ligand) complex are shown in FIGS. 7 and 8. FIG. 7 shows the ligand atoms, which are predominantly on the phenyl moiety, that are involved in the HOMO. FIG. 8 shows the ligand atoms, which are predominantly on the quinolinyl moiety, that are involved in the LUMO. Substituents attached to atoms of the ligand involving the HOMO influence the HOMO by either stabilizing (lowering its energy) or destabilizing it (raising its energy). Accordingly, substituents that are activating, and attached to a carbon atom contributing to the HOMO, can raise the HOMO energy level, thereby decreasing the HOMO-LUMO gap and increasing the wavelength of emission (red-shift, bathochromic shift). Similarly, substituents that are deactivating (largely electron-withdrawing) can lower the HOMO energy level, thereby increasing the HOMO-LUMO gap and decreasing the wavelength of emission (blue-shift, hypsochromic shift). Conversely, substituents that are activating, and attached to a carbon atom contributing to the LUMO, can raise the LUMO energy level, thereby increasing the HOMO-LUMO gap and decreasing the wavelength of emission. Similarly, substituents that are deactivating, and attached to a carbon atom contributing to the LUMO, can lower the LUMO energy level, thereby decreasing the HOMO-LUMO gap and increasing the wavelength of emission. In addition, deactivating groups can be substituted on ligand atoms that are not involved in either the HOMO or LUMO (i.e., nodes) generally resulting in blue-shifted emission color.

As is evident, emission color can be deliberately red-shifted or blue-shifted upon selection of ligand and substitution site in order to obtain a desired hue. Accordingly, the present invention encompasses methods of increasing the wavelength of emission, such as can be measured by a photoluminescence maximum for a compound of the present invention (or electroluminescence maximum for a device comprising a compound of the present invention), relative to emission from a reference compound having the same structure, but having hydrogen(s) at the substitution site(s). In some embodiments, the methods comprise choosing substituents $R^1$, $R^2$, $R^3$, $R^4$, $R^5$, $R^6$, $R^7$, $R^8$, $R^9$, or $R^{10}$ such that at least one of these is an activating group that influences the HOMO energy level of the compound. Alternatively, or in addition, at least one of the substituents can be a deactivating group that influences the LUMO energy level of said compound. Example 2, infra, details results from a representative method of the invention. Similarly, the present invention further includes methods of decreasing the wavelength of emission, such as can be measured by a photoluminescence maximum for a compound of the present invention (or electroluminescence maximum for a device comprising a compound of the present invention), relative to emission from a reference compound having the same structure, but having hydrogen (s) at the substitution site(s). In some embodiments, the method comprises choosing substituents $R^1$, $R^2$, $R^3$, $R^4$, $R^5$, $R^6$, $R^7$, $R^8$, $R^9$, or $R^{10}$ such that at least one of these substituents is a deactivating group that influences the HOMO energy level of the compound. Alternatively, or in addition, at least one of the substituents can be an activating group that influences the LUMO energy level of the compound.

In some embodiments, the methods of increasing emission wavelength can comprise selection of substituents such that $R^3$ is an activating group. Conversely, choosing $R^3$ as a deactivating group can relate to methods according to the present invention for decreasing emission wavelength. In other embodiments, methods for increasing emission wavelength can comprise choosing $R^{10}$ as a deactivating group. Similarly, methods for decreasing emission wavelength can comprise choosing $R^{10}$ as an activating group.

Figure 3:
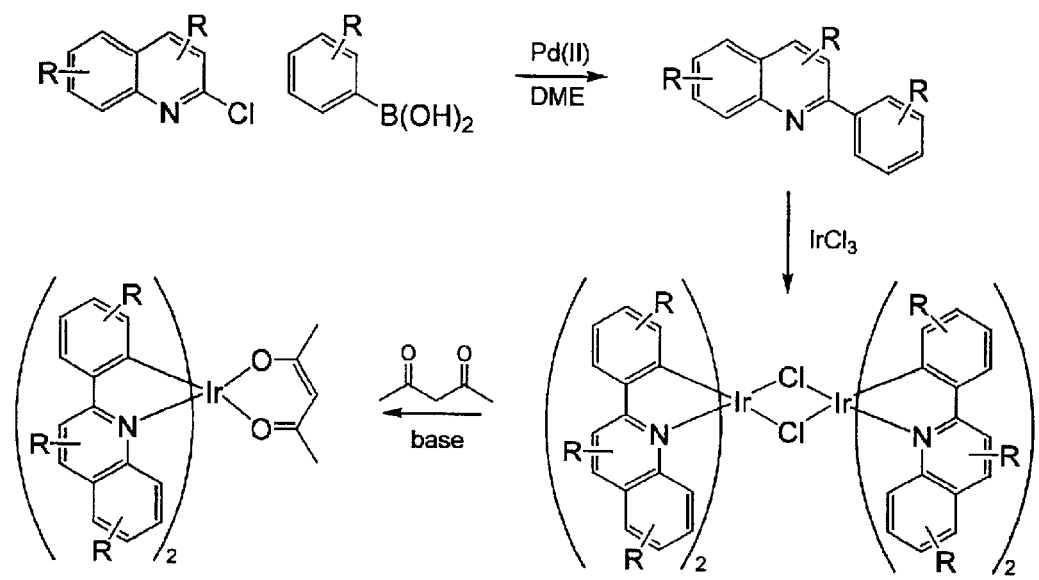
FIG. 3 shows a schematic for preparing compounds of the present invention.
Figure 4:
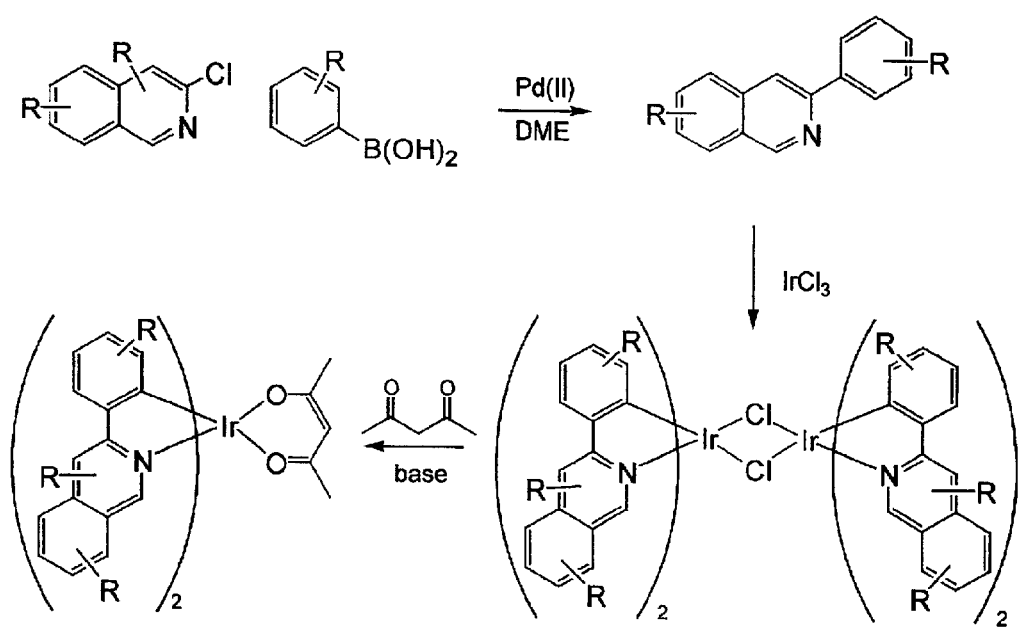
FIG. 4 shows a schematic for preparing compounds of the present invention.

Processes for preparing compounds described herein are also embodied by the present invention. A synthesis schematic for compounds of Formula I is shown in FIG. 3. A synthesis schematic for compounds of Formula II is shown in FIG. 4. Compounds of Formula III can be made similarly. Phenylquinolinato ligands (L) having desired substitution according to the present invention can be made using the general procedure of coupling phenyl boronic acid having desired substitution with chloroquinoline (e.g., 2-chloroquinoline, 3-chloroisoquinoline, or 2-chloroisoquinoline) also having desired substitution. Coupling procedures can be, for example, conducted under Suzuki conditions in the presence of palladium(II) (see, e.g., Miyaura, et al., *Chem. Rev.* 1995, 2457). The quinoline (or isoquinoline) and boronic acid starting materials can be obtained from commercial sources or synthesized by methods known in the art. For example, 3-chloroisoquinoline can be made according to the procedures described in Haworth, R. D., et al., *J Chem. Soc.*, 1948, 777.

Phenylquinoline ligands (L) having desired substitution can be coordinated to a metal atom by, for example, contacting the ligands with a metal halide complex. Metal halide complexes include compounds comprising at least one metal coordinated to one or more halide ligands. Metal halide complexes can be of the Formula $M(Q)_q$ where Q is a halide ligand and q is the number of halide ligands. For example, q can range from about 2 to about 6. For the preparation of iridium-containing compounds, the metal halide complex can be $IrCl_3$. This and other metal halide complexes are well known in the art and commercially available. Under sufficient time and conditions, the contacting can result in the formation of a metal-containing intermediate, having mixed coordination of halide and phenylquinoline ligands L. In some embodiments, the metal atom of the intermediate can coordinate to at least one L. In other embodiments, the metal atom of the intermediate can coordinate two L. In further embodiments, the intermediate can be polynuclear, comprising, for example, more than one metal atom and bridging halide ligands. When the metal halide complex is $IrCl_3$, the metal-containing intermediate can be an iridium dimer complex, having, for example, the structure $L_2Ir(\mu$-$Cl)_2IrL_2$. Any remaining halide ligands of the intermediate, including bridging halides, can be replaced by ligand substitution with one or more ancillary ligands, such as represented by $A^1$ and $A^2$ in any of the Formulas I to IV, to yield compounds of the present invention. $A^1$ and $A^2$ can be monodentate ligands or are combined to form a single bidentate ligand. For example, 2,4-pentanedione in the presence of base can replace coordinated halide ligands in the metal-containing intermediate to give acetylacetonato complexes of the present invention. Syntheses of exemplary compounds of the present invention are provided in Examples 3–15.

The compounds described herein can be used as emitters in organic light emitting devices. Accordingly, the compounds can be present in an emissive layer (i.e., a layer from which light is primarily emitted) of a such device. The emissive layer can be, for example, a layer consisting essentially of one or more compounds of the present invention. The present compounds can also be present as dopants. For example, an emissive layer can comprise host material doped with one or more of the present compounds. The host material can comprise any compound, including organic and organometallic compounds, suitable in an emissive layer in an OLED. For example, organic host material can comprise BCP (bathocuproine or 2,9-dimethyl-4,7-diphenyl-1,10-phenanthroline), CBP (4,4'-N,N'-dicarbazole biphenyl), OXD7 (1,3-bis(N,N-t-butylphenyl)-1,3,4-oxadiazole), TAZ (3-phenyl-4-(1'-naphthyl)-5-phenyl-1,2,4-triazole), NPD (4,4'-bis[N-(1-naphthyl)-N-phenyl-amino]biphenyl), and the like. Other host material can comprise CuPc (copper phthalocyanine), $Alq_3$ (aluminum tris(8-hydroxyquinolate)), BAlq ((1,1'-biphenyl)-4-olato)bis(2-methyl-8-quinolinolato N1,O8)aluminum), and the like. Other materials that can be included in an emissive layer, in addition to the compounds of the present invention, include Irppy (tris(2-phenylpyridinato-N,C2')iridium(III)), FIrpic (bis(2-(4,6-difluorophenyl)pyridinato-N,C2')iridium(III)(picolinate)), and other metal complexes such as those described in U.S. Ser. Nos. 09/274,609, now abandoned; 09/311,126, now abandoned; 09/452,346, now abandoned; 09/637,766; 60/283,814; and U.S. Ser. No. 09/978,455, filed Oct. 16, 2001, entitled "Organometallic Compounds and Emission-Shifting Organic Electrophosphorescence" to Lamansky, et al., each of which is incorporated herein by reference in its entirety. As dopants, the present compounds can be present in the emissive layer, such as in host material, in amounts of from about 1 to about 20 wt %, about 5 to about 15 wt %, about 5 to about 10 wt %, or other similar ranges.

Accordingly, the present invention includes compositions comprising compounds of the present invention. In some embodiments, compositions comprise at least one compound of the present inventions and a further compound suitable for use in an OLED. For example, further compounds can include any of the host materials mentioned above. Additionally, further compounds can include other emitters or metal complexes, such as FIrpic, Irppy, and other complexes mentioned above and incorporated by reference.

Devices comprising the present compounds have superior properties as compared with known devices. For example, high external quantum and luminous efficiencies can be achieved in the present devices. Device lifetimes are also generally better than, or at least comparable to, some of the most stable fluorescent devices reported. Data for some devices according to the present invention are provided in Example 1.

Devices of the present invention can emit at any color. Some devices of the present invention, such as, for example, those comprising iridium, can be red emitters. Red devices of the invention can have electroluminescence maxima of from about 550 to about 700 nm. Similarly, color index coordinates (CIE) for red devices of the invention can range from about 0.5 to about 0.8 for x and about 0.2 to about 0.5 for y. In some embodiments, devices, such as, for example, red devices, can have external quantum efficiencies greater than about 4%, 5%, 6%, 7%, 8%, 10%, 12%, or higher at a brightness greater than about 10, 100, 1000 cd/m², or more.

Typical devices are structured so that one or more layers are sandwiched between a hole injecting anode layer and an electron injecting cathode layer. The sandwiched layers have two sides, one facing the anode and the other facing the cathode. Layers are generally deposited on a substrate, such as glass, on which either the anode layer or the cathode layer may reside. In some embodiments, the anode layer is in contact with the substrate. In some embodiments, for example when the substrate comprises a conductive or semi-conductive material, an insulating material can be inserted between the electrode layer and the substrate. Typical substrate materials, that may be rigid, flexible, transparent, or opaque, include glass, polymers, quartz, sapphire, and the like.

In some embodiments, devices of the present invention comprise further layers in addition to a layer comprising the present compounds (e.g., an emissive layer). For example, in addition to the electrodes, devices can include any one or more hole blocking layers, electron blocking layers, exciton blocking layers, hole transporting layers, electron transporting layers, hole injection layers, or electron injection layers. Anodes can comprise an oxide material such as indium-tin oxide (ITO), Zn—In—$SnO_2$, $SbO_2$, or the like, and cathodes can comprises a metal layer such as Mg, Mg:Ag, or LiF:Al. Among other materials, the hole transporting layer (HTL) can comprise triaryl amines or metal complexes such as those described in U.S. Ser. Nos. 60/317,540 which is incorporated herein by reference in its entirety. Similarly, the electron transporting layer (ETL) can comprise, for example, aluminum tris(8-hydroxyquinolate) ($Alq_3$) or other suitable materials. Additionally, a hole injection layer can comprise, for example, 4,4',4"-tris(3-methylphenylphenylamino)triphenylamine (MTDATA) or polymeric material such as poly(3,4-ethylenedioxythiophene) (PEDOT), or metal complex such as, for example, copper phthalocyanine (CuPc), or other suitable materials. Hole blocking, electron blocking, and exciton blocking layers can comprise, for example, BCP, BAlq, and other suitable materials such as FIrpic or other metal complexes described in U.S. Ser. Nos. 60/317,540 which is incorporated herein by reference in its entirety. Compounds of the present invention can also be included in any of the above mentioned layers.

Light emitting devices of the present invention can be fabricated by a variety of techniques well known to those skilled in the art. Small molecule layers, including those comprised of neutral metal complexes, can be prepared by vacuum deposition, organic vapor phase deposition (OVPD), such as disclosed in U.S. Ser. No. 08/972,156, filed Nov. 17, 1997, now U.S. Pat. No. 6,337,102, which is incorporated herein by reference in it its entirety, or solution processing such as spin coating. Polymeric films can be deposited by spin coating and chemical vapor deposition (CVD). Layers of charged compounds, such as salts of charged metal complexes, can be prepared by solution methods such a spin coating or by an OVPD method such as disclosed in U.S. Pat. No. 5,554,220, which is incorporated herein by reference in its entirety. Layer deposition generally, although not necessarily, proceeds in the direction of the anode to the cathode, and the anode typically rests on a substrate. Devices and techniques for their fabrication are described throughout the literature and in, for example, U.S. Pat. Nos. 5,703,436; 5,986,401; 6,013,982; 6,097,147; and 6,166,489, each of which is incorporated herein by reference in its entirety. For devices from which light emission is directed substantially out of the bottom of the device (i.e., substrate side), a transparent anode material such as ITO may be used as the bottom electron. Since the top electrode of such a device does not need to be transparent, such a top electrode, which is typically a cathode, may be comprised of a thick and reflective metal layer having a high electrical conductivity. In contrast, for transparent or top-emitting devices, a transparent cathode may be used such as disclosed in U.S. Pat. Nos. 5,703,436 and 5,707,745, each of which is incorporated herein by reference in its entirety. Top-emitting devices may have an opaque and/or reflective substrate, such that light is produced substantially out of the top of the device. Devices can also be fully transparent, emitting from both top and bottom.

Transparent cathodes, such as those used in top-emitting devices preferably have optical transmission characteristics such that the device has an optical transmission of at least about 50%, although lower optical transmissions can be used. In some embodiments, devices include transparent cathodes having optical characteristics that permit the devices to have optical transmissions of at least about 70%, 85%, or more. Transparent cathodes, such as those described in U.S. Pat. Nos. 5,703,436 and 5,707,745, typically comprise a thin layer of metal such as Mg:Ag with a thickness, for example, that is less than about 100 Å. The Mg:Ag layer can be coated with a transparent, electrically-condutive, sputter-deposited, ITO layer. Such cathodes are often referred to as compound cathodes or as TOLED (transparent-OLED) cathodes. The thickness of the Mg:Ag and ITO layers in compound cathodes may each be adjusted to produce the desired combination of both high optical transmission and high electrical conductivity, for example, an electrical conductivity as reflected by an overall cathode resistivity of about 30 to 100 ohms per square. However, even though such a relatively low resistivity can be acceptable for certain types of applications, such a resistivity can still be somewhat too high for passive matrix array OLED pixels in which the current that powers each pixel needs to be conducted across the entire array through the narrow strips of the compound cathode.

Light emitting devices of the present invention can be used in a pixel for an electronic display. Virtually any type of electronic display can incorporate the present devices. Displays can include computer monitors, televisions, personal digital assistants, printers, instrument panels, bill boards, and the like. In particular, the present devices can be used in flat panel displays and heads-up displays.

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

EXAMPLES

Example 1

Compound and Device Properties

Substituted phenylquinolinato iridium(III) acetylacetonate compounds 2 to 13 and comparative compound 1 (see FIGS. 1 and 2) were characterized and used as emissive dopants in organic light emitting devices having the structure glass/ITO/CuPc/NPD/CPB:dopant/BAlq/$Alq_3$/LiF/Al. Photophysical properties of the compounds and devices were surprisingly remarkable as illustrated in Table I.

Device emissions ranged from orange to deep red. The highest efficiency was obtained from an orange-red device comprising compound 11. External quantum efficiencies greater than 8% and luminous efficiencies higher than 20 cd/A were routinely obtained at the brightness level of a full color display, i.e., 10–1000 cd/m². These efficiencies are almost an order of magnitude higher than for known red-emitting fluorescent devices such as the DCJTB devices reported in Hatwar, et al., *Proceedings of the 10th International Workshop of Inorganic and Organic Electroluminescence*, December, 2000, Hamamatsu, Japan, p. 31. Lifetime studies under constant current drive showed half-lives extrapolated to longer than 5,000 hours at initial brightness of 300 cd/m².

TABLE 1

| No. | CIE (x, y) in $CH_2Cl_2$ | CIE (x, y) in device | External Quantum Efficiency @ 10 mA/cm² | Brightness Cd/A @ 10 mA/cm² | Power Efficiency Lm/W 10 mA/cm² | Photoluminscence maximum (nm) |
|---|---|---|---|---|---|---|
| 1 | (0.62, 0.38) | (0.62, 0.38) | 10.3 | 17.4 | 4.8 | 606 nm |
| 2 | (0.60, 0.40) | (0.58, 0.40) | 6.8 | 13.2 | 3.9 | 602 nm |
| 3 | (0.65, 0.35) | (0.65, 0.34) | 6.4 | 6.8 | 2.0 | 626 nm |
| 4 | (0.61, 0.39) | (0.61, 0.38) | 8.3 | 14 | 3.9 | 608 nm |
| 5 | (0.70, 0.30) | (0.70, 0.30) | 5.8 | 2.0 | 0.53 | 656 mn |
| 6 | (0.58, 0.42) | (0.58, 0.42) | 8.4 | 17.3 | 4.6 | 591 nm |
| 7 | (0.65, 0.35) | (0.58, 0.40) | 3.0 | 4.4 | 1.3 | 632 nm |
| 8 | (0.56, 0.44) | (0.54, 0.45) | 4.9 | 11.4 | 3.3 | 590 nm |
| 9 | (0.59, 0.41) | (0.56, 0.42) | 5.1 | 10.4 | 3.0 | 592 nm |
| 10 | (0.55, 0.45) | (0.54, 0.46) | 6.6 | 16.8 | 4.7 | 585 nm |
| 11 | (0.59, 0.41) | (0.60, 0.40) | 11.8 | 22.9 | 6.8 | 598 nm |
| 12 | (0.65, 0.35) | (0.65, 0.35) | 9.8 | 11 | 3.2 | 626 nm |
| 13 | (0.68, 0.32) | (0.67, 0.33) | 10.5 | 8.1 | 2.4 | 626 nm |

Example 2

Tuning Emission Color

By attaching an activating substituent to a ligand atom involved in the HOMO of a compound of the present invention, a 50 nm red-shift in the photoluminscence maximum was observed relative to an unsubstitued reference compound. For example, the photoluminescence maximum for compound 5 (see FIG. 1) is reported as 656 nm in Table 1. This is a 50 nm increase relative to reference compound 1 (see FIG. 1), having a photoluminescence maximum at 606 nm (Table 1). MO calculations predicted that the $R^3$ substituent contributes to the HOMO (see FIG. 7). Indeed, substitution at $R^3$ with activating methoxy results in a distinct red-shift in the photoluminescence spectrum as compared with the reference compound 1 where $R^3$ is hydrogen.

Example 3

Synthesis of Bis(2-phenylquinoline)iridium(III) Acetylacetonate (Compound 1)

Step 1

2-Phenylquinoline (6.0 g, 29 mmol) and iridium(III) chloride hydrate (5.2 g, 14 mmol) were added to a flask containing 80 mL of 2-methoxyethanol and 20 mL of distilled water. The reaction mixture was heated to reflux and stirred under a nitrogen atmosphere for 24 hours. After cooling, the red precipitate formed was vacuum filtered and washed first with absolute ethanol followed by hexanes. The dichloro-bridged dimer was dried in a vacuum oven to give 6.7 g (38% yield). The product was not purified any further but used directly in the next step.

Step 2

The dichloro-bridged dimer (6.7 g, 5.3 mmol) was added to 200 mL of a solution a containing 2-methyoxyethanol (150 mL). Sodium carbonate (5.6 g, 53 mmol) and 2,4-pentanedione (5.3 g, 53 mmol) were added to the reaction mixture. The reaction mixture was heated to 105° C. and stirred under nitrogen for 18 hours. After the reaction was cooled to room temperature, the precipitate was vacuum filtered. The filtered product was added to 500 mL of distilled water and stirred for 10 minutes. The red precipitate was vacuum filtered, washed with additional distilled water, followed by several rinses with absolute ethanol followed by hexanes to give bis(2-phenylquinoline)iridium(III) acetylacetonate (3.0 g). The desired product was purified by vacuum sublimation.

Example 4

Synthesis of Bis[2-(2-fluorophenyl)quinoline] iridium(III) Acetylacetonate (Compound 2)

Step 1

2-Chloroquinoline (4.9 g, 30 mmol), 2-fluorophenylboronic acid (5.0 g, 36 mmol) and $K_2CO_3$ (12 g) were dissolved in the solvent mixture of 50 mL ethylene glycol dimethyl ether and 75 mL water. To the stirred solution was added 1.7 g tetrakis(triphenylphosphine) palladium(O) and the mixture refluxed under $N_2$ for 20 hours. The reaction mixture was cooled and the water extracted with methylene chloride three times. The combined organic phase was washed with portions of brine. The organic layer was then dried with anhydrous sodium sulfate, filtered, and evaporated of solvent. The crude material was purified on a silica gel column to give 2-(2-fluorophenyl)quinoline (6.4 g, 96% yield).

Step 2

2-(2-Fluorophenyl)quinoline (6.2 g, 28 mmol) was dissolved in the solvent mixture of 90 mL 2-methoxyethanol and 30 mL of water. To the stirred solution was added 4.9 g iridium(III) chloride trihydrate. The mixture refluxed under $N_2$ overnight. The solution was cooled down and filtered. The reddish solid was washed with ethanol twice and dried in vacuum to give 2-(2-fluorophenyl)quinoline Ir dimer (5.2 g).

Step 3

2-(2-Fluorophenyl)quinoline Ir dimer (5.2 g) was added to 90 mL 2-methoxyethanol and to the stirred solution was added 1.0 g 2,4-pentanedione and 4.2 g sodium carbonate. The mixture was heated at 100° C. with stirring overnight under $N_2$. The cooled mixture was then filtered to give bis[2-(2-fluorophenyl)quinoline]iridium(III) acetylacetonate (3.0 g) which was further purified by vacuum sublimation.

Example 5

Synthesis of Bis[2-(2-methylphenyl)quinoline] iridium(III) Acetylacetonate (Compound 3)

Step 1

To a 500 mL round bottom flask was added, 2-chloroquinoline (4.7 g, 31 mmol), o-tolylphenyl boronic acid (4.7 g, 36 mmol) into 100 mL of ethylene glycol dimethyl ether. Sodium carbonate (8.9 g, 84 mmol) was dissolved into 50 mL of distilled water and added to the reaction mixture. After the addition of 0.1 mole % of triphenylphosphine (0.8 g) followed by 0.025 mol % of palladium(II) acetate (0.2 g). the reaction was heated under a nitrogen atmosphere for 4 hours. After cooling, additional ethyl acetate was added and the aqueous layer discarded. The organic layer was washed with a saturated solution of brine. The organic layer was dried over magnesium sulfate, filtered and the solvent removed by a rotary evaporator. The crude yellow oil was purified by column chromatography using a silica gel column and 20% ethyl acetate/hexanes as the eluants. The pure product was collected, combined and concentrated to give 2-(2-methylphenyl)quinoline (6.0 g, 75% yield).

Step 2

2-(2-Methylphenyl)quinoline (6.0 g, 27 mmol) and iridium(III) chloride trihydrate (5.2 g, 15 mmol) were added to a flask containing a solution of 2-ethyoxyethanol (80 mL) and water (20 mL). The reaction mixture was heated to reflux and stirred under a nitrogen atmosphere for 20 hours. After cooling the dark red precipitate that formed was filtered and washed with ethanol followed by hexanes to give the dichloro-bridged dimer (6.4 g).

Step 3

The above dichloro-bridged dimer (2.7 g, 20 mmol) and 2,4-pentanedione (2.0 g, 20 mmol) were added to dichloromethane and a solution of potassium carbonate (5.5 g, 50 mL) and refluxed overnight. The reaction mixture was cooled and the solids removed by vacuum filtration. The filtrate was concentrated and the crude product purified by a silica gel column using ethyl acetate and hexanes as the eluants to give bis[2-(2-methylphenyl)quinoline]iridium(III) acetylacetonate (1.5 g) which was further purified by sublimation.

Example 6

Synthesis of Bis[2-(2-methoxyphenyl)quinoline] iridium(III) Acetylacetonate (Compound 4)

Step 1

2-Chloroquinoline (2.45 g, 15.0 mmol), o-methoxyphenylboronic acid (2.73 g, 18.0 mmol,) and potassium carbonate (5.59 g, 40.4 mmol) were dissolved in 40 mL ethylene glycol dimethyl ether and 20 mL of water. To the stirred solution was added tetrakis (triphenylphosphine)palladium(O) (1.04 g, 0.89 mmol) and the entire mixture was allowed to reflux under a $N_2$ atmosphere for 20 hours. The cooled reaction mixture was then removed of water. Additional ethyl acetate (150 mL) was added and the solvent was washed three times using 100 mL portions of brine. The organic layer was dried with anhydrous sodium sulfate, filtered, and the solvent concentrated. The residue purified via column chromatography using 50% ethyl acetate/hexanes as the eluents to give 2-(o-methoxyphenyl)quinoline.

Step 2

2-(o-Methoxyphenyl)quinoline (5.85 g, 23.1 mmol) and iridium(III) chloride trihydrate (4.07 g, 11.5 mmol) were dissolved into a solution containing 2-methoxyethanol (100 mL) and 20 mL of distilled water. The entire mixture was allowed to reflux at 100° C. for 24 hours under a $N_2$ atmosphere. The solution was allowed to cool to room temperature where the reddish solid was collected and washed with ethanol twice and dried in vacuum to give 2-(o-methoxyphenyl)quinoline-dichloro-bridged iridium dimer (4.53 g, 53.6% yield).

Step 3

2-(o-Methoxyphenyl)quinoline-dichloro-bridged iridium dimer (3.49 g, 2.38 mmol) and 2,4-pentanedione (0.57 g, 5.72 mmol) was added to a solution containing 2-methoxyethanol (150 mL) and sodium carbonate (2.53 g, 23.8 mmol). The mixture was allowed to stir at 105° C. for 24 hours under $N_2$ atmosphere. The precipitate was collected after the reaction mixture was cooled and the solids washed with water (200 mL) for 30 minutes (with stirring action). The water mixture was vacuum filtered and the solids rinsed with ethanol. The product was dried in vacuum to give bis[2-(2-methoxyphenyl)quinoline]iridium(III) acetylacetonate (1.80 g, 47.4%). The crude product was purified by sublimation.

Example 7

Synthesis of Bis[2-(3-methoxyphenyl)quinoline] iridium(III) Acetylacetonate (Compound 5)

Step 1

2-Chloroquinoline (5.38 g, 32.9 mmol), and 3-methoxyphenylboronic acid (6.0 g, 39.5 mmol) were dissolved in 130 mL of ethylene glycol dimethyl ether. To the solution was added 44 mL of water of a 2M $K_2CO_3$ solution followed by triphenylphosphine (0.86, g 3.29 mmol) and palladium(II) acetate (0.184 g, 0.82 mmol,). The reaction mixture was stirred at reflux under $N_2$ atmosphere overnight. The reaction mixture was cooled and the aqueous layer discarded. An additional 200 mL of ethyl acetate was added and the solvent was washed twice with 150 mL portions of brine. The organic layer was dried with anhydrous sodium sulfate, filtered and evaporated. The crude product was purified by column chromatography on a silica gel column using 20% ethyl acetate/hexanes as the eluants. The pure fraction was collected and the solvent was reduced to give 2-(3-methoxyphenyl)quinoline (7.90 g, 94.8% yield).

Step 2

2-(3-Methoxyphenyl)quinoline (7.5 g, 29.6 mmol) and iridium(III) chloride trihydrate (5.22 g, 14.8 mmol) were stirred in 120 mL of 2-methoxyethanol and 30 mL water at reflux for 24 hours under $N_2$ atmosphere. The mixture was cooled to room temperature, filtered and the reddish precipitate collected was rinsed with ethanol. The solids were then dried in vacuum to give the dichloro-bridged dimer (6.09 g, 56.2% yield).

Step 3

2-(3-Methoxyphenyl)quinoline Ir dimer (4.0 g, 2.73 mmol), 2,4-pentanedione (0.68 g, 6.83 mmol) and $Na_2CO_3$ (2.89 g 27.3 mmol) were stirred in 100 mL of 2-methoxyethanol. The reaction mixture was stirred at room temperature under $N_2$ atmosphere for a period of 20 hours. The precipitate was filtered and the remaining solids washed with 300 mL using water. The product was collected by vacuum filtration and the solids rinsed with hexanes. The crude solid was purified on a silica gel column using 50% ethyl acetate and hexanes as the eluants to give bis[2-(3-methoxyphenyl)quinoline]iridium(III) acetylacetonate (1.35 g, 34% yield). The product was further purified by sublimation.

Example 8

Synthesis of Bis[2-(4-methoxyphenyl)quinoline] iridium (III) Acetylacetonate (Compound 6)

Step 1

2-Chloroquinoline (5.0 g, 31 mmol) and 4-methoxyphenylboronic acid (5.5 g, 36 mmol) were dissolved in a solvent mixture containing 40 mL ethylene glycol dimethyl ether and 60 mL water containing 12.0 g $K_2CO_3$. To the stirred solution was added 1.6 g tetrakis (triphenylphosphine)palladium(O) and the mixture refluxed under $N_2$ overnight. The cooled reaction mixture was then removed of water, extracted with methylene chloride three times. The combined organic phase was washed with portions of brine and then dried with anhydrous sodium sulfate, filtered, and evaporated of solvent to give 2-(p-methoxyphenyl)quinoline (5.0 g) after column chromatography (20% ethyl acetate in hexane).
Step 2

2-(p-Methoxyphenyl)quinoline (4.6 g, 20 mmol) was dissolved in the solvent mixture of 120 mL 2-methoxyethanol and 40 mL water and to the stirred solution was added iridium(III) chloride trihydrate (3.4 g, 10 mmol). The mixture was refluxed under $N_2$ atmosphere overnight. The solution was cooled down and filtered. The reddish solid was then washed with ethanol twice and dried in vacuum to give 2-(p-methoxyphenyl)quinoline Ir dimer (3.6 g).
Step 3

2-(p-Methoxyphenyl)quinoline Ir dimer (3.3 g) was added to 80 mL 2-methoxyethanol and to the stirred solution was added 2,4-pentanedione (0.59 g) and sodium carbonate (2.5 g). The mixture was heated at 30° C. with stirring for 24 hours under $N_2$. The cooled mixture was then filtered to give bis[2-(4-methoxyphneyl)quinoline]iridium (III) acetylacetonate (1.5 g) and further purified by sublimation.

Example 9

Synthesis of Bis[2-(2-trifluoromethylphenyl) quinoline]iridium(III) Acetylacetonate (Compound 7)

Step 1

2-Chloroquinoline (7.2 g, 44.0 mmol), 2-trifloromethylphenylboronic acid (10.0 g, 52.6 mmol), triphenylphosphine (1.16g, 4.4 mmol), palladium acetate (0.26 g, 1.16 mmol) and 12 mL of a 2M solution of potassium carbonate were added together to 50 mL of ethylene glycol dimethyl ether (DME). The reaction mixture was heated under a nitrogen atmosphere and refluxed 17 hours. The mixture was cooled to room temperature and the aqueous phase was separated from the organic phase. The aqueous phase was extracted with 2×100 mL of ethyl acetate. The combined organic extracts were washed using 1×150 mL of DI water, 1×150 mL of brine and dried over magnesium sulfate. The collected filtrate was evaporated to a crude oil. The crude product was purified by column chromatography using 80% hexanes and 20% ethyl acetate as the eluants to give 2-(3-trifluorophenyl)quinoline (6.3 g).
Step 2

2-(2-Trifluoromethylphenyl)quinoline (2.5 g, 12.1 mmol) from step 1, iridium(III) chloride (1.6 g, 4.53 mmol) were added to 60 mL of 2-ethoxyethanol and 20 mL of DI water and heated under nitrogen at reflux(100° C.) for 20 hours. The mixture was then cooled to room temperature and vacuum filtered. The filtered crude product was then washed with 2×50 mL of ethanol and 1×50 mL of hexane and dried in a vacuum oven to yield 2.9 g (47.9%) of dimer complex.
Step 3

The dimer complex (3.4 g, 2.2 mmol) 2,4-pentanedione (5.5 g, 5.5 mmol) and sodium carbonate (2.33 g, 22 mmol) were added to 70 mL of 2-ethoxyethanol and heated under nitrogen at reflux (124° C.) for 17 hours. The mixture was then cooled to room temperature and vacuum filtered. The filtered crude product was then added to 500 mL of DI water and stirred for ten minutes. The filtered crude product was then vacuum filtered and washed 2×150 mL of ethanol and 1×150 mL of hexane. The collected product was dried in a vacuum oven to give bis[2-(2-trifluoromethylphenyl) quinoline]iridium(III) acetylacetonate (0.6 g, 27.6%) which was further purified by vacuum sublimation.

Example 10

Synthesis of Bis[2-(3-trifluoromethylphenyl) quinoline]iridium(III) Acetylacetonate (Compound 8)

Step 1

2-Chloroquinoline (1.44 g, 8.8 mmol), and 3-trifloromethylphenylboronic acid (2.0 g, 10.5 mmol) were added to 10 mL of ethylene glycol dimethyl ether (DME) and 12 ml of a 2M solution of potassium carbonate. This was followed by the addition of triphenylphosphine (0.23 g, 0.88 mmol) and palladium acetate (0.05 g, 0.22 mmol). The reaction mixture was heated at reflux (80° C.) under a nitrogen atmosphere for 17 hours. The mixture was then cooled to room temperature and the aqueous phase extracted 2×30 mL with ethyl acetate. The combined organic extractions were then washed with water followed by brine. The organics were dried over magnesium sulfate. The collected filtrate was then evaporated to give 2-(3-trifluorophenyl) quinoline (2.0 g, 83.3%) as a white solid.
Step 2

2-(3-Trimethylphenyl)quinoline (2.0 g, 7.3 mmol) from step 1, and iridium(III) chloride trihydrate (1.3 g, 3.68 mmol) were added to a solution containing 40 mL of 2-ethoxyethanol and 10 mL of DI water. The reaction was heated under nitrogen at reflux (100° C.) 26 hours. The mixture was then cooled to room temperature and vacuum filtered. The filtered crude product was washed with 2×50 mL of ethanol and 1×50 mL of hexanes and dried in a vacuum oven to give the dichloro-bridged dimer (1.77 g, 73.8% yield).
Step 3

The dimer complex from step 2 above (1.77 g, 1.2 mmol), a 10-fold molar excess of 2,4-pentanedione (1.19 g, 11.9 mmol) and a 20-fold excess of sodium carbonate (2.53 g, 23.7 mmol) were added to 40 mL of 2-ethoxyethanol and heated under nitrogen at reflux (124° C.) for 18 hours. The mixture was cooled to room temperature and the precipitate was vacuum filtered. The crude product was added to 400 mL of DI water and stirred for ten minutes, vacuum filtered and washed using 2×50 mL of ethanol and 1×50 mL of hexanes. The collected product was dried in a vacuum oven to give bis[2-(3-trifluoromethylphenyl)quinoline]iridium (III) acetylacetonate (1.7 g).

Example 11

Synthesis of Bis[2-(4-trifluoromethylphenyl) quinoline]iridium(III) Acetylacetonate (Compound 9)

Step 1

2-Chloroquinoline (1.56 g, 9.5 mmol), 4-trifloromethylphenylboronic acid (2.17 g, 11.4 mmol), triphenylphosphine (0.25 g, 0.95 mmol), palladium acetate (0.05 g, 0.22 mmol) and 12 mL of a 2M solution of potassium carbonate were added to 10 mL of ethylene glycol dimethyl ether (DME) and heated under nitrogen at reflux (80° C.) for 18 hours. The mixture was then cooled to room temperature and the aqueous phase was separated from the organic phase. The aqueous phase was then extracted with 2×30 mL of ethyl acetate. The combined organic extractions were then extracted with 1×50 mL portion of DI water and 1×50 mL portion of brine and dried over magnesium sulfate. The collected filtrate was then evaporated to (2.47 g, 94.7%) a crystalline solid.

Step 2

2-(4-Trimethylphenyl)quinoline (2.47 g, 9.0 mmol) from step 1, iridium(III) chloride (1.59 g, 4.5 mmol) were added to 50 mL of 2-ethoxyethanol and 15 mL of water and heated under nitrogen at reflux (100° C.) for 16 hours. The mixture was cooled to room temperature and vacuum filtered. The filtered crude product was then washed with 2×50 mL of ethanol and 1×50 mL of hexane and dried in a vacuum oven to yield (1.65 g, 49.2%) of the desired dimer complex.

Step 3

The dimer complex from step 2 above (1.65 g, 1.1 mmol), a 10-fold molar excess of 2,4-pentanedione (1.11 g, 11.9 mmol), and a 20-fold excess of sodium carbonate (2.36 g, 22.2 mmol) were added to 40 mL of 2-ethoxyethanol and heated under nitrogen at reflux (124° C.) for 17 hours. The mixture was cooled to room temperature and vacuum filtered. The filtered crude was added to 400 mL of water and stirred for ten minutes. The filtered crude product was vacuum filtered and washed 2×50 mL of ethanol and 1×50 mL of hexanes. The collected product was dried in a vacuum oven to give bis[2-(4-trifluoromethylphenyl)quinoline]iridium(III) acetylacetonate (1.0 g). The product was purified further by vacuum sublimation.

Example 12

Synthesis of Bis[2-(2,4-difluorophenyl)quinoline] iridium(III) acetylacetonate (Compound 10)

Step 1

2-Chloroquinoline (1.20 g, 12.2 mmol), 2,4-difluorophenylboronic acid (2.32 g, 14.7 mmol), were added to 10 mL of ethylene glycol dimethyl ether (DME) and 12 mL of a 2 M solution of potassium carbonate. Triphenylphosphine (0.32 g, 1.2 mmol) and palladium acetate (0.069 g, 0.3 mmol) were added to the stirred reaction mixture and refluxed for 17 hours under a nitrogen atmosphere. The mixture was cooled to room temperature and the aqueous phase was separated from the organic phase. The aqueous phase was extracted with 2×30 mL of ethyl acetate. The combined organic extracts were washed first with distilled water followed by brine. The solvent was dried over magnesium sulfate and concentrated to give 2-(2,4-difluorophenyl)quinoline (2.9 g, 98.6%) as a white solid.

Step 2

2-(2,4-Difluorophenyl)quinoline (2.9 g, 12.1 mmol) from step 1 above and iridium(III) chloride (2.1 g, 5.96 mmol) were added to 40 mL of 2-ethoxyethanol and 10 mL of DI water and heated under nitrogen at reflux for 16 hours. The mixture was cooled to room temperature and the crude product removed by vacuum filtration. The filtered crude product was washed with 2×50 mL of ethanol and 1×50 mL of hexanes and dried in a vacuum oven to yield (2.3 g, 51.3%) of the dimer complex.

Step 3

The dimer complex from step 2 above (2.3 g, 1.6 mmol) a 10-fold molar excess of 2,4-pentanedione (1.6 g, 16 mmol) and a 20-fold excess of sodium carbonate (3.4 g, 32 mmol) were added to 40 mL of 2-ethoxyethanol and heated under nitrogen at reflux (124° C.) for 17 hours. The mixture was then cooled to room temperature and vacuum filtered. The filtered crude was then added to 400 mL of DI water and stirred for ten minutes. The filtered crude was then vacuum filtered and washed 2×50 mL of ethanol and 1×50 mL of hexane. The collected product was dried in a vacuum oven to give a bis[2-(2,4-difluorophenyl)quinoline]iridium(III) acetylacetonate (2.1 g).

Example 13

Synthesis of Bis(2-phenyl-4-methylquinoline) iridium(III) Acetylacetonate (Compound 11)

Step 1

2-Chloro-4-methylquinoline (5.0 g, 30 mmol) and phenyl boronic acid (4.4 g, 36 mmol) were dissolved into 100 mL of ethylene glycol dimethyl ether. To the stirred reaction was added triphenylphosphine (0.8 g) and palladium(II) acetate, followed by 50 mL of a 2 M solution of potassium carbonate. The reaction was refluxed for 16 hours. After cooling, the aqueous layer was discarded and additional ethyl acetate added. The organics were washed with a saturated solution of sodium chloride and separated. The organic layer was dried over magnesium sulfate, concentrated, and purified on a silica gel column using 20% ethyl acetate and hexanes as the eluants. The pure fractions were combined and concentrated to give 2-phenyl-4-methylquinoline (4.0 g, 61% yield) as an oil.

Step 2

2-Phenyl-4-methylquinoline (4.0 g, 18 mmol) and iridium (III) chloride trihydrate (3.2 g, 9 mmol) were dissolved into a solution containing 80 mL of 2-methoxyethanol and 20 mL of water. The reaction mixture was refluxed for 18 hours and cooled to room temperature. The red/brown precipitate was collected by vacuum filtration and washed once with absolute ethanol followed by hexanes to give the dichloro-bridged dimer (3.0 g, 25% yield).

Step 3

The dichloro-bridged dimer (3.0 g, 2.3 mmol) and 2,4-pentanedione (2.3 g, 23 mmol) were dissolved into a solution containing 100 mL of 2-methoxyethanol and sodium carbonate (4.8 g in 50 mL). The reaction mixture was heated to reflux and stirred under a nitrogen atmosphere for 17 hours. The reaction mixture was cooled and the red precipitate was collected by vacuum filtration to give bis[2-(2,4-difluorophenyl)quinoline]iridium(III) acetylacetonate (2.1 g) as a red solid. The material was further purified by vacuum sublimation.

Example 14

Synthesis of Bis(2-phenyl-3-methylquinoline) iridium(III) Acetylacetonate (Compound 12)

Step 1

2-Chloro-3-methylquinoline (5.43 g, 30.6 mmol), phenylboronic acid (4.47 g, 36.7 mmol), Pd(II) acetate (0.17 g, 0.76 mmol), and triphenylphosphine (0.80 g, 3.06 mmol) were dissolved in 100 mL DME. To the stirred solution was added $K_2CO_3$ (11.4 g dissolved into 41 mL $H_2O$). The entire mixture was allowed to stir at reflux for 18 hours under $N_2$ atmosphere. The cooled mixture was then removed of water, enriched with 150 mL of ethyl acetate, extracted three times from brine, dried over anhydrous sodium sulfate, filtered and evaporated of solvent. The crude liquid was then purified on a silica gel column using 20% ethyl acetate/hexanes. The purest fractions were combined to give 2-phenyl-3-methylquinoline (6.42 g, 95.8% yield).

Step 2

3-Methyl-2-phenylquinoline (5.80 g, 26 mmol) was stirred in 100 mL 2-methoxyethanol/25 mL $H_2O$ and to the stirred solution was added iridium (III) chloride hydrate (4.9 g, 13 mmol). The reaction mixture was allowed to stir under $N_2$ atmosphere at 100° C. for 24 hours. The solids were collected on a filter, and rinsed with ethanol to give the dichloro-bridged dimer (2.72 g, 30.9% yield).

Step 3

3-Methyl-2-phenylquinoline Ir dimer (2.72 g) was stirred in 80 mL 2-methoxyethanol and to the solution was added sodium carbonate (2.72 g) and 2,4-pentanedione (1.02 g). This was allowed to stir for 24 hours under N$_2$ atmosphere. The reaction mixture was filtered and the solids washed with water. The solids were then filtered again and rinsed with hexanes. The amount collected gave bis(2-phenyl-3-methylquinoline)iridium(III) acetylacetonate (0.85 g, 29.8% yield). This material was purified by vacuum sublimation.

Example 15

Synthesis of Bis(phenylisoquinoline)iridium(III) Acetylacetonate (Compound 13)

Step 1

1-Chloroisoquinoline (5.0 g, 30 mmol) and phenylboronic acid (4.5 g, 37 mmol) was dissolved into 100 mL of ethylene glycol dimethyl ether, followed by the addition of triphenylphosphine (0.7 g, 3 mmol) and Pd(II) acetate (0.17 g, 0.75 mmol). The reaction mixture was refluxed for 16 hours. The reaction mixture was cooled and the aqueous layer discarded. Additional ethyl acetate was added and the solvent was washed with a saturated solution of sodium chloride, dried over magnesium sulfate and concentrated to give 1-phenylisoquinoline (5.0 g, 79% yield)

Step 2

1-Phenylisoquinoline (5.0 g, 24 mmol) and iridium(III) chloride trihydrate (4.5 g, 12 mmol) was add to a solution containing 80 mL of 2-methoxyethanol and 20 mL of water. The reaction was heated to reflux and stirred under a nitrogen atmosphere for 12 hours. The reaction mixture was cooled and the red/brown precipitate was collected by vacuum filtration and washed once with hexanes. The dichloro-bridged dimer (5.3 g, 30% yield) was dried and used directly in the next step.

Step 3

The dichloro-bridged dimer (2.0 g, 1.6 mmol) and 2,4-pentanedione (1.6 g, 16 mmol) were added to 100 mL of 2-methoxyethanol to which a solution of sodium carbonate (3.34 g, 50 mL) was added and the reaction mixture heated to reflux. The reaction mixture was cooled after 16 hours and the crude product collected by vacuum filtration to give bis(phenylisoquinoline)iridium(III) acetylacetonate (1.0 g). The crude material was purified by vacuum sublimation.

As those skilled in the art will appreciate, numerous changes and modifications can be made to the preferred embodiments of the invention without departing from the spirit of the invention. It is intended that all such variations fall within the scope of the invention. Throughout this specification, various groupings are employed to conveniently describe constituent variables of compounds and groups of various related moieties. It is specifically intended that each occurrence of such groups throughout this specification include every possible subcombination of the members of the groups, including the individual members thereof.

It is intended that each of the patents, applications, and printed publications mentioned in this patent document be hereby incorporated by reference in its entirety.

What is claimed is:

1. A compound of the formula:

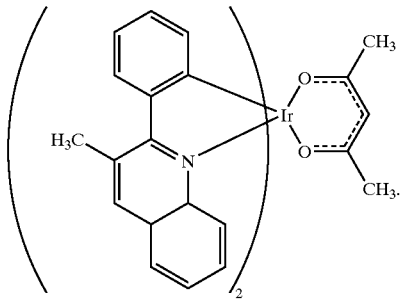

2. An organic light emitting device comprising an anode, a cathode and an emissive layer, wherein the emissive layer is between the anode and the cathode, and wherein the emissive layer comprises a compound of the formula:

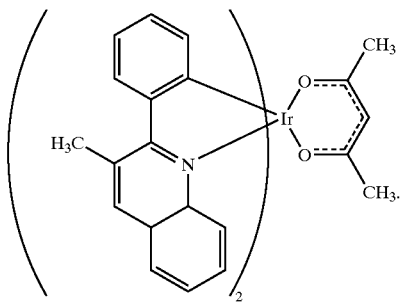

* * * * *

UNITED STATES PATENT AND TRADEMARK OFFICE
CERTIFICATE OF CORRECTION

PATENT NO. : 6,835,469 B2
DATED : December 28, 2004
INVENTOR(S) : Kwong et al.

It is certified that error appears in the above-identified patent and that said Letters Patent is hereby corrected as shown below:

Column 2,
Line 24, after "Nos." change "0/9274,609" to -- 09/274,609 --;
Line 25, before "09/452,346" insert -- 09/311,126, now abandoned -- and Column 7,
Line 14, change "bexafluoroacetylacetonate" to -- hexafluoroacetylacetonate --.

Signed and Sealed this

Tenth Day of May, 2005

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,835,469 B2 |
| APPLICATION NO. | : 09/981496 |
| DATED | : December 28, 2004 |
| INVENTOR(S) | : Kwong et al. |

It is certified that error appears in the above-identified patent and that said Letters Patent is hereby corrected as shown below:

Column 26, line 65, change "glass/ITO/CuPc/NPD/CPB:dopant/BAlq/Alq$_3$/LiF/Al" to -- glass/ITO/CuPc/NPD/CBP:dopant/BAlq/Alq$_3$/LiF/Al --

Signed and Sealed this

Seventh Day of November, 2006

JON W. DUDAS
*Director of the United States Patent and Trademark Office*